US011344590B2

(12) United States Patent
Moshitzky et al.

(10) Patent No.: US 11,344,590 B2
(45) Date of Patent: May 31, 2022

(54) TRANSGENIC MICROALGAE AND USE THEREOF FOR ORAL DELIVERY OF PROTEINS

(71) Applicant: TRANSALGAE ISRAEL LTD., Rehovot (IL)

(72) Inventors: Shiri Moshitzky, Tel Aviv (IL); Doron Eisenstadt, Kfar Saba (IL); Guy Levi, Jerusalem (IL); Ofra Chen, Rehovot (IL)

(73) Assignee: TRANSALGAE ISRAEL LTD., Rehovot (IL)

( * ) Notice: Subject to any disclaimer, the term of this patent is extended or adjusted under 35 U.S.C. 154(b) by 520 days.

(21) Appl. No.: 15/791,924

(22) Filed: Oct. 24, 2017

(65) Prior Publication Data

US 2018/0036357 A1 Feb. 8, 2018

Related U.S. Application Data

(63) Continuation of application No. 14/628,891, filed on Feb. 23, 2015, now Pat. No. 9,827,280, which is a continuation of application No. PCT/IL2013/050712, filed on Aug. 21, 2013.

(60) Provisional application No. 61/781,103, filed on Mar. 14, 2013, provisional application No. 61/692,240, filed on Aug. 23, 2012.

(51) Int. Cl.
| | | |
|---|---|---|
| *A61K 36/02* | (2006.01) | |
| *C12N 1/13* | (2006.01) | |
| *A23K 10/16* | (2016.01) | |
| *A23K 10/18* | (2016.01) | |
| *A23K 50/80* | (2016.01) | |
| *A61K 38/22* | (2006.01) | |
| *C07K 14/575* | (2006.01) | |
| *C07K 14/61* | (2006.01) | |
| *C07K 14/46* | (2006.01) | |
| *A23K 50/20* | (2016.01) | |
| *A23K 50/10* | (2016.01) | |
| *A61K 38/27* | (2006.01) | |
| *A23K 50/75* | (2016.01) | |
| *C12N 1/12* | (2006.01) | |

(52) U.S. Cl.
CPC ............ *A61K 36/02* (2013.01); *A23K 10/16* (2016.05); *A23K 10/18* (2016.05); *A23K 50/75* (2016.05); *A23K 50/80* (2016.05); *A61K 38/22* (2013.01); *A61K 38/27* (2013.01); *C07K 14/461* (2013.01); *C07K 14/61* (2013.01); *C12N 1/12* (2013.01); *C07K 2319/04* (2013.01); *C07K 2319/05* (2013.01); *C07K 2319/06* (2013.01)

(58) Field of Classification Search
None
See application file for complete search history.

(56) References Cited

U.S. PATENT DOCUMENTS

| | | | | |
|---|---|---|---|---|
| 5,643,877 A | * | 7/1997 | Zohar | ............. C07K 7/23 514/10.3 |
| 7,410,637 B2 | | 8/2008 | Sayre | |
| 8,282,915 B2 | | 10/2012 | Sayre | |
| 2003/0066107 A1 | | 4/2003 | Xue et al. | |
| 2006/0263820 A1 | | 11/2006 | Kyle | |
| 2007/0118916 A1 | * | 5/2007 | Puzio | ............. C12N 15/8214 800/278 |
| 2007/0148166 A1 | | 6/2007 | Wu et al. | |
| 2009/0098149 A1 | | 4/2009 | Sayre et al. | |
| 2011/0014708 A1 | | 1/2011 | Tsai et al. | |
| 2011/0081706 A1 | | 4/2011 | Schlesinger et al. | |
| 2011/0165635 A1 | | 7/2011 | Copenhaver et al. | |
| 2013/0065314 A1 | | 3/2013 | MacMillan | |
| 2014/0154806 A1 | | 6/2014 | Schneider et al. | |
| 2014/0234904 A1 | | 8/2014 | Herbert et al. | |

FOREIGN PATENT DOCUMENTS

| | | |
|---|---|---|
| CN | 1330718 A | 1/2002 |
| CN | 1778932 A | 5/2006 |
| CN | 101960013 A | 1/2011 |
| CN | 102559735 A | 7/2012 |
| EP | 1 541 036 A1 | 6/2005 |
| JP | 6-505870 A | 7/1994 |
| JP | 2012-500640 A | 1/2012 |
| JP | 6275143 B2 | 2/2018 |
| WO | 92/16618 A1 | 10/1992 |
| WO | WO 9216618 | * 10/1992 |

(Continued)

OTHER PUBLICATIONS

Bajpai et al, Developments of Cyanobacteria for Nano-Marine Drugs: Relevance of Nanoformulations in Cancer Therapies, Mar. Drugs 2018, 16, 179 pp. 1-23.*
Charoonnart et al, Applications of Microalgal Biotechnology for Disease Control in Aquaculture, Biology 2018, 7, 24 pp. 1-14.*
Kim et al, Stable Integration and Functional Expression of Flounder Growth Hormone Gene in Transformed Microalga, *Chlorella ellipsoidea*, Mar. Biotechnol. 4, 63-73, 2002.*
Li et al, Transgenic microalgae as a non-antibiotic bactericide producer to defend against bacterial pathogen infection in the fish digestive tract, Fish & Shellfish Immunology, 2009, pp. 316-325.*

(Continued)

*Primary Examiner* — Maria Marvich
(74) *Attorney, Agent, or Firm* — J.A. Lindeman & Co. PLLC

(57) ABSTRACT

Transgenic microalgae expressing at least one exogenous biologically active protein. The protein-expressing microalgae are used for the oral delivery of the biologically active protein to the target organism in its intact and functional form. The exogenous protein, expressed in algae, is characterized by being biologically active, exerting at least one specific activity having a beneficial effect on the subject consuming the algae. The transgenic microalgae are used as animal food for aquatic or land animals welfare or as food supplement for human healthcare.

17 Claims, 18 Drawing Sheets

Specification includes a Sequence Listing.

(56) References Cited

FOREIGN PATENT DOCUMENTS

| WO | 97/39106 A1 | 10/1997 |
| --- | --- | --- |
| WO | 01/98335 A2 | 12/2001 |
| WO | 02/076391 A2 | 10/2002 |
| WO | 2005112994 A1 | 12/2005 |
| WO | 2008/027235 A1 | 3/2008 |
| WO | 2011/063284 A1 | 5/2011 |
| WO | 2012/030759 A1 | 3/2012 |

OTHER PUBLICATIONS

Zaslavskaia et al, Transformation of the diatom *Phaeodactylum tricornutum* (Bacillariophyceae) with a variety of selectable marker and reporter genes, J of Phycology, 2000, pp. 379-386.*

Kumar et al, Bioengineering of Microalgae: Recent Advances, Perspectives, and Regulatory Challenges for Industrial Application, Frontiers in Bioengineering and Biotechnology, 2020, pp. 1-31.*

Shanks et al, Are animal models predictive for humans? Philosophy, Ethics, and Humanities in Medicine, 2009, pp. 1-20.*

Niccolai et al, Microalgae of interestas food source: Biochemical composition and digestibility, 2019, pp. 1-9.*

Galas et al, Comparative Structural and Functional Analyses of the Fusiform, Oval, and Triradiate Morphotypes of Phaeodactylum tricornutum Pt3 Strain, Front. Plant Sci., Apr. 12, 2021, pp. 1-15.*

Jiang et al., (2002) Membrane anchors for vacuolar targeting: application in plant bioreactors. Trends Biotechnol 20(3): 99-102.

Apt et al., (1996) Stable nuclear transformation of the diatom Phaeodactylum tricornutum. Mol Gen Genet 252(5): 572-579.

Bowler et al., Phaeodactylum tricomutum CCAP 1055/1 endo-1,3-beta-glucosidase, mRNA; XM_002181285.1. From: http://www.ncbi.nlm.nih.gov/nuccore/XM_002181285.1; retrieved on Aug. 15, 2016; 2 pages; Nature, vol. 456, No. 7219, pp. 239-244, (2008).

Dreesen et al., (2010) Heat-stable oral alga-based vaccine protects mice from *Staphylococcus aureus* infection. J Biotechnol 145(3): 273-280.

Fawley et al. (2004) A Simple and Rapid Technique for the Isolation of DNA from Microalgae. J Phycol 40: 223-225.

Gregory et al., (2013) Alga-produced cholera toxin-Pfs25 fusion proteins as oral vaccines. Appl Environ Microbiol 79(13): 3917-3925.

Grzebyk et al., (2003) The Mesozoic radiation of eukaryotic algae: the portable plastid hypothesis. J Phycol 39: 259-267.

Guillard et al. (1962) Studies of marine planktonic diatoms. I. Cyclotella nana Hustedt, and Detonula confervacea (cleve) Gran. Can J Microbiol 8: 229-239.

Hempel et al., (2011) Algae as protein factories: expression of a human antibody and the respective antigen in the diatom Phaeodactylum tricornutum. PLoS One 6(12): e28424.

Jha et al., (2007) Comparative effect of live food and manured treatments on water quality and production of ornamental carp, *Cyprinus carpio* var. *koi* L., during winter, summer, monsoon and post-monsoon growout experiments in concrete tanks. Journal of Applied Ichthyology 23(1): 87-92.

Khan et al., (2012) Using storage organelles for the accumulation and encapsulation of recombinant proteins. Biotechnol J 7(9): 1099-1108.

Kilian et al. (2005) Identification and characterization of a new conserved motif within the presequence of proteins targeted into complex diatom plastids. Plant J 41(2): 175-183.

Kim et al., (2002) Stable integration and functional expression of flounder growth hormone gene in transformed microalga, *Chlorella ellipsoidea*. Mar Biotechnol (NY) 4(1): 63-73.

Kwon et al., (2013) Oral delivery of human biopharmaceuticals, autoantigens and vaccine antigens bioencapsulated in plant cells. Adv Drug Deliv Rev 65(6): 782-799.

Lin et al., (2007) An oral nervous necrosis virus vaccine that induces protective immunity in larvae of grouper (*Epinephelus coioides*). Aquaculture 268(1-4): 265-273.

Miyamoto et al., (1984) Identification of the second gonadotropin-releasing hormone in chicken hypothalamus: evidence that gonadotropin secretion is probably controlled by two distinct gonadotropin-releasing hormones in avian species. Proc Natl Acad Sci U S A 81(12): 3874-3878.

Rasala et al., (2014) Enhanced genetic tools for engineering multigene traits into green algae. PLoS One 9(4): e94028; 8 pages.

Reinders et al., (2012) Evolution of plant sucrose uptake transporters. Front Plant Sci 3: 22; 12 pages.

Richter et al., (2000) Production of hepatitis B surface antigen in transgenic plants for oral immunization. Nat Biotechnol 18(11): 1167-1171.

Siripornadulsil et al., (2007) Microalgal Vaccines. In: León R., Galván A., Fernández E. (eds) Transgenic Microalgae as Green Cell Factories. Advances in Experimental Medicine and Biology, vol. 616. Springer, New York, NY; pp. 122-128.

Specht et al., (2010) Micro-algae come of age as a platform for recombinant protein production. Biotechnol Lett 32(10): 1373-1383.

Tague et al., (1990) A short domain of the plant vacuolar protein phytohemagglutinin targets invertase to the yeast vacuole. Plant Cell 2(6): 533-546.

Xiang et al., (2013) Vacuolar protein sorting mechanisms in plants. FEBS J 280(4): 979-993.

Database UniprotKB/TrEMBL (online), I Nov. 1996 (Nov. 1, 1996). The ER chaperone BiP from the diatom Phaeodactylum, Uniprot accession No. Q41074. URL: http://www.uniprot.org/uniprot/Q41074.

Becker and Hoef-Emden (2009) Evolution of vacuolar targeting in algae. Botanica Marina 52(2): 117-128.

Bowler et al., Endo-1,3-beta-glucosidase [Phaeodactylum tricornutum CCAP 1055/1]. GenBank Accession XP_002181321; pp. 1-2 (2009); 2 pages.

Kermode (1996) Mechanisms of Intracellular Protein Transport and Targeting in Plant Cells. Critical Reviews in Plant Sciences 15: 285-423.

Murray et al., (2002) Expression of biotin-binding proteins, avidin and streptavidin, in plant tissues using plant vacuolar targeting sequences. Transgenic Res 11(2): 199-214.

Nakamura and Matsuoka (1993) Protein targeting to the vacuole in plant cells. Plant Physiol 101(1): 1-5.

Ravindran (2013) Feed enzymes: The science, practice, and metabolic realities. Journal of Applied Poultry Research 22(3): 628-636.

* cited by examiner

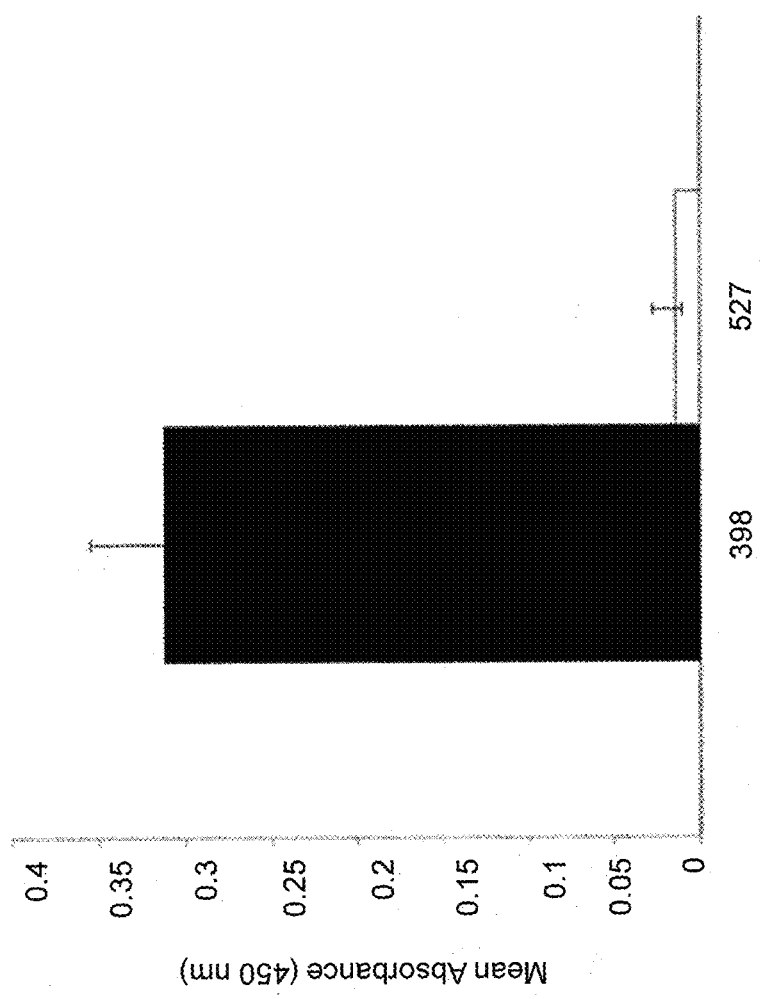

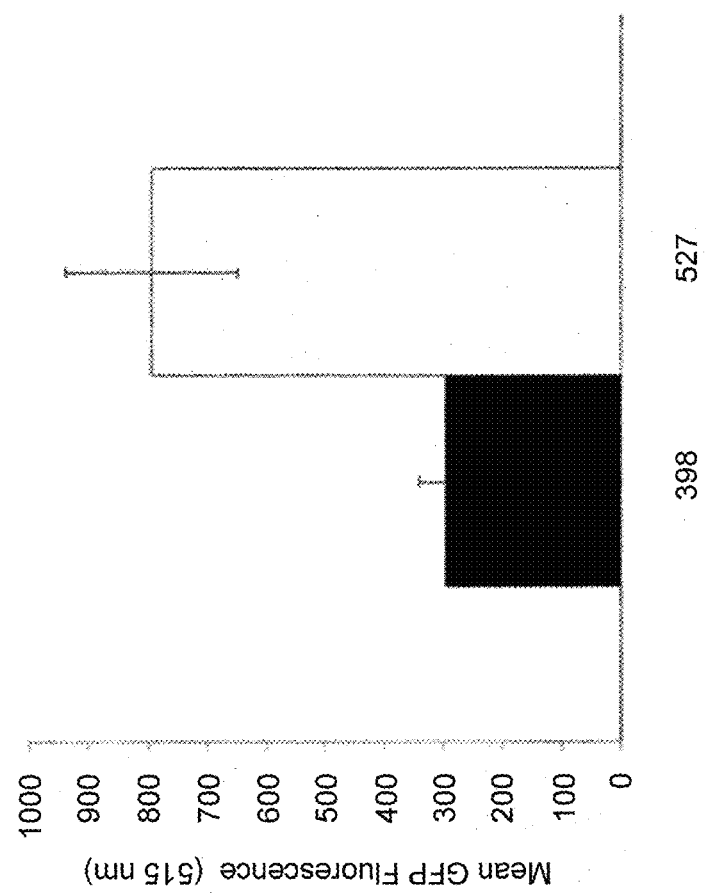

TRANSGENIC MICROALGAE AND USE THEREOF FOR ORAL DELIVERY OF PROTEINS

CROSS-REFERENCE TO RELATED APPLICATIONS

This application is a continuation of U.S. patent application Ser. No. 14/628,891, filed Feb. 23, 2015, now U.S. Pat. No. 9,827,280, which is a continuation of PCT Patent Application No. PCT/IL2013/050712, filed Aug. 21, 2013, which claims priority to U.S. Provisional Application No. 61/781,103, filed Mar. 14, 2013, and to U.S. Provisional Application No. 61/692,240 filed Aug. 23, 2012.

SEQUENCE LISTING

The Sequence Listing submitted in text format (.txt) filed on Oct. 24, 2017, named "SequenceListing.txt", created on Oct. 24, 2017, 41.5 KB, is incorporated herein by reference.

FIELD OF THE INVENTION

The present invention relates to transgenic microalgae expressing exogenous biologically active proteins and use thereof for oral delivery of the biologically active proteins to animals and humans.

BACKGROUND OF THE INVENTION

Bioactive proteins are essential for the function of cells of living organisms, and are responsible for most of the activities of the cell including catalysis of metabolic processes, communication, defense, movement, and transport. Oral delivery of bioactive proteins is typically required for two principal purposes: delivery of therapeutic proteins and delivery of proteins that have nutritional or another beneficial effect on animals, including humans.

The growing demand for food over the world, particularly for animal protein, together with the awareness towards environmental impacts of animal growth, requires the development of sophisticated agricultural management tools that would improve the productivity and weight gain of terrestrial as well as aquatic farm animals. Development of aquacultures for the growth of marine animals including fish, crustaceans and mollusks is of particular importance, as marine animal are considered as an healthier source for proteins.

However, aquaculture is still not a completely efficient system for growing marine animals and fish in particular. Typically, fish require a relatively long period of time to reach an acceptable size and weight. Furthermore, many breeds of fish mature in an inefficient manner, such that problems may occur in the fish population, resulting in loss of a portion of the population due to excessively slow growth, poor morphology (for ornamental fish) and so forth. Furthermore, in the artificial aquaculture environment, the aquatic animals are more susceptible to infectious diseases and, when disease does occur, it can spread rapidly through entire populations with high mortality.

There is thus a need for routes to administer therapeutic or nutritional proteins to terrestrial as well as aquatic farm animals that are not costly and do not require laborious efforts. Oral delivery of therapeutic or nutritional proteins to humans is also highly desirable, as this mode of administration does not require professional manpower and significantly increases the patient compliance to the prescribed dose. The biological activity of a protein depends on its sequence and/or conformation, which must be preserved until the protein reaches its target of activity. For successful oral delivery, proteins should be protected from chemical and enzymatic degradation that may occur during processing the proteins into food or a feed composition and through the delivery via the animal's gastrointestinal tract. In addition, the protein should overcome structural barriers that preclude entry into the animal or access to the target destination.

Microalgae (single cell alga or phytoplankton) represent the largest, but most poorly understood, kingdom of microorganisms on the earth. Like plants are to terrestrial animals, the microalgae represent the natural nutritional base and primary source of all the phytonutrients in the aquatic food chain. Expression of recombinant proteins in algae has been reported, and various methods are available for production of exogenous proteins within the algae cells, particularly within the cell plastid. International (PCT) Application Publication No. WO 2011/063284 discloses methods of expressing therapeutic proteins in photosynthetic organisms, including prokaryotes such as cyanobacteria and eukaryotes such as alga and plants. Transformation of eukaryotes is preferably into the plastid genome, typically into the chloroplast genome. The Application discloses expression of particular therapeutic proteins within algae cells.

Various attempts have been made to use microalgae as delivery means for proteins. For example, International (PCT) Application Publication No. WO 01/98335 discloses delivery systems and methods for delivering a biologically active protein to a host animal. The systems and methods provided include obtaining an algal cell transformed by an expression vector, the expression vector comprising a nucleotide sequence coding for the biologically active protein, operably linked to a promoter. In one illustrated embodiment, the biologically active protein is an antigenic epitope and upon administration to the animal the algal cell induces an immune response in the host animal.

International (PCT) Application Publication No. WO 2002/076391 discloses the use of microbial cells which are used as feed components in aquaculture or agriculture, and which also contain exogenous peptides, proteins, and/or antibodies, which will convey resistance or immunity to viral or bacterial pathogens or otherwise improve the health and performance of the species consuming said microbial cells. The microbial cells can be yeast, fungi, bacteria, or algae. The proteins and/or antibodies may be expressed inside the microbial cells by direct genetic modification of the microbe itself, or by the infection of the microbe with a virus that has been altered to express the protein of interest.

International (PCT) Application Publication No. WO 2008/027235 discloses methods for prevention, amelioration or treatment of a disease or disorder in an aquatic animal, by feeding the aquatic animal directly or indirectly with genetically modified micro algae that expresses a recombinant molecule that specifically targets one or more key epitopes of a pathogen that infects the aquatic animal.

U.S. Patent Application Publication No. 2011/0014708 discloses method of producing a foreign desired gene product in algae that comprises weakening or removing the algae cell wall by a protein enzyme solution to facilitate the gene transfer and a feed composition comprising the transgenic algae or its offspring. The invention also provides a modified nucleic acid for expressing bovine lactoferricin (LFB) in algae.

However, there is still an unmeet need for and it would be highly advantageous to have an oral delivery system that is easy for production and use, maintains the biological activity of the protein and facilitate absorption of the biologically active protein systemically.

SUMMARY OF THE INVENTION

The present invention provides an algal based platform for oral delivery of biologically active proteins to an organism, providing for the systemic absorption of the biologically active protein in its active form. Particularly, the present invention provides transgenic microalgae expressing at least one exogenous protein within a predetermined subcellular compartment. The protein-expressing microalgae are used as animal food or food additive applicable for feeding aquatic animals and land animals as well as for food supplement for humans. The exogenous protein is characterized by being biologically active, exerting at least one specific activity having a beneficial effect on the target organism.

The present invention is based in part on the unexpected discovery that the expressed protein remains active and exerts its specific activity having a beneficial effect when the algae are orally consumed by aquatic animals (including fish and crustaceans) as well as by land animals (including mice and poultry). Typically, the protein remains in its intact form. Without wishing to be bound by any particular theory or mechanism of action, the preserved protein activity may be attributed to its localization within the intact microalga, such that the microalgal cell serves as a natural encapsulation material protecting the protein from being degraded in the animal's gastrointestinal tract and/or acidic stomach. According to certain typical embodiments of the present invention, the protein is expressed in a microalgal subcellular compartment, particularly in the vacuole.

Thus, according to one aspect, the present invention provides a transgenic eukaryotic microalga comprising an expression cassette comprising at least one transcribable polynucleotide encoding a biologically active exogenous protein, wherein the biologically active exogenous protein is expressed within a subcellular compartment of the microalga cell.

The subcellular compartment in which the protein is expressed depends on the microalga species, the type of the protein expressed and the animal species to be fed. According to certain embodiments, the subcellular compartment is selected from the group consisting of vacuole, endoplasmic reticulum, Golgi system, lysosome and peroxisome. Each possibility represents a separate embodiment of the present invention.

According to certain exemplary embodiments, the exogenous protein is expressed within the microalga cell vacuole. According to these embodiments, the expression cassette further comprises a polynucleotide encoding a vacuole targeting peptide. According to some embodiments, the peptide targeting the exogenous protein into the vacuole is a short vacuole leader sequence having the amino acid sequence set forth in SEQ ID NO:4. According to other embodiments, the polynucleotide encoding the short vacuole leader peptide comprises the nucleic acid sequence set forth in SEQ ID NO:18.

According to certain other exemplary embodiments, the exogenous protein is expressed within the microalga cell endoplasmic reticulum (ER). According to these embodiments, the expression cassette further comprises a polynucleotide encoding an ER targeting peptide. According to some embodiments, the peptide targeting the exogenous protein into the ER is a *Phaeodactylum tricornutum* endoplasmic reticulum (Bip) leader sequence having the amino acid sequence set forth in SEQ ID NO:2. According to other embodiments, the polynucleotide encoding the ER leader peptide comprises the nucleic acid sequence set forth in SEQ ID NO:16.

Various microalgae species can be used according to the teachings of the present invention. According to certain embodiments, the microalga used according to the teachings of the present invention is a marine microalga. According to certain embodiments, the microalga is selected from the group consisting of, but not restricted to, *Phaeodactylum tricornutum; Dunaliella* spp.; *Nannochloropsis* spp. including *Nannochloropsis oculata, Nannochloropsis salina, Nannochloropsis gaditana; Nannochioris* spp., *Tetraselmis* spp. Including *Tetraselmis suecica, Tetraselmis chuii; lsochtysis galbana; Pavlova* spp.; *Amphiprora hyaline; Chaetoceros muelleri;* and *Neochloris oleoabundans.* Each possibility represents a separate embodiment of the present invention.

According to certain specific embodiments, the microalga is selected from the group consisting of *Phaeodactylum tricornutum, Nannochloris* spp., *Nannochloropsis* spp. and *Dunaliella* spp.

According to other specific embodiments, the microalga is *Phaeodactylum tricornutum.*

The transgenic microalgae of the present invention can be transformed to express any protein having an effect on the target animal consuming same.

According to certain embodiments, the molecular weight of the expressed protein is up to 150 kDa. According to other embodiments, the molecular weight of the expressed protein is up to 140 kDa, 130 kDa, 120 kDa or 110 kDa. According to other embodiments the molecular weight of the expressed protein is in the range of 1-100 kDa. According to certain exemplary embodiments the molecular weight if the expressed protein is in the range of 1-50 kDa.

According to certain embodiments, the protein has a beneficial effect on at least one of the growth, development and survival of the consuming animal. Each possibility represents a separate embodiment of the present invention. According to other embodiments, the protein has a therapeutic effect on the animal consuming the transgenic microalgae.

According to yet additional embodiments, the animal is an aquatic animal and the expressed protein affects the aquatic animal morphology. According to some embodiments, the protein has an effect of the aquatic body deformation. Body deformation includes but is not limited to any morphological irregularity, any type of body asymmetry, irregular body shape, irregular fin shape, irregular tail shape; irregular body/fin area, length or width ratios; irregular body/tail area, length or width ratios; irregular tail/fin area, length or width ratios; or irregularities in any body part. According to certain currently specific embodiments, the expressed protein reduces or eliminates body deformation of the aquatic animal.

According to further certain embodiments, the transgenic microalga expresses a hormone. According to some embodiments, the animal is an aquatic animal and the hormone is selected from the group consisting of a growth hormone, appetite inducing hormone and spawning hormone. Each possibility represents a separate embodiment of the present invention.

According to certain currently specific embodiments, the expressed protein is fish growth hormone. According to some embodiments, the fish growth hormone is Salmon growth hormone having the amino acid sequence set forth in SEQ ID NO:12. According to certain specific embodiments, the fish growth hormone is encoded by the polynucleotide having the nucleic acid sequence set forth in SEQ ID NO:1.

According to additional embodiments, the expressed protein is spawning hormone having the amino acid sequence set forth in SEQ ID NO:24 (Accession No.: P68072). According to certain specific embodiments, the spawning hormone is encoded by the polynucleotide having the nucleic acid sequence set forth in SEQ ID NO:25.

According to yet further embodiments, the expressed protein is appetite inducing hormone having the amino acid sequence set forth in SEQ ID NO:20. According to certain specific embodiments, the appetite hormone is encoded by the polynucleotide having the nucleic acid sequence set forth in SEQ ID NO:21.

According to additional aspect, the present invention provides an edible composition comprising transgenic microalgae of the present invention. According to some embodiments, the edible composition is an animal food composition. According to exemplary embodiments, the animal food composition is for feeding aquatic animals. According to yet other embodiments, the edible composition is for human consumption. As described hereinabove, the edible composition is used for oral delivery of biologically active proteins. According to some embodiments, particularly when the edible composition is for animal consumption, the edible composition consists essentially of the transgenic algae. According to further embodiments, the edible composition consists of the transgenic algae. The edible composition may be used per se or as an additive to animal or human food.

According to an additional aspect the present invention provides a method of delivering a biologically active protein to an animal, the method comprising orally administering to an animal subject transgenic eukaryotic microalgae comprising an expression cassette comprising at least one transcribable polynucleotide encoding the biologically active protein, wherein said biologically active protein is expressed within a subcellular compartment of the microalga cell.

According to certain embodiments, the subcellular compartment is selected from the group consisting of vacuole, endoplasmic reticulum, *Golgi* system, lysosome and peroxisome. Each possibility represents a separate embodiment of the present invention.

According to certain specific embodiments, the exogenous protein is expressed within the microalga cell vacuole. According to other specific embodiments the exogenous protein is expressed within the microalga cell endoplasmic reticulum.

According to some embodiments, the transgenic eukaryotic microalgae are administered within an animal or human food composition.

According to a further aspect the present invention provides a method for improving at least one of the animal growth rate, growth pattern, reproductive health status, survival or any combination thereof, comprising administering to the animal an effective amount of the transgenic microalgae of the present invention or a composition comprising same, thereby improving the growth rate and/or the growth pattern and/or the survival and/or the reproductive health status of said animal.

According to certain embodiments the animal subject is a land animal or an aquatic animal. The land animal may optionally be any animal grown for food or for a non-food purpose (the latter including but not limited to work animals, pets and the like), including but not limited to cows, pigs, horses, dogs, cats, mice, rats, rabbits, guinea pigs, poultry and the like. The aquatic animal may optionally be any animal grown for food or for a non-food purpose (the latter including but not limited to ornamental, and the like), including but not limited to fish, crustaceans, and corals. According to additional embodiments the animal subject is a human.

Other objects, features and advantages of the present invention will become clear from the following description and drawings.

BRIEF DESCRIPTION OF THE FIGURES

FIG. 16 demonstrates the absorption of the algae-expressed fGH into the fish blood. Tilapia fish were force fed with acuole-GFP expressing algae (construct 527) or with vacuole-fGH expressing algae (construct 398). Level of fGH in the blood was determined using ELISA directed specifically against the recombinant fGH. Results are shown as mean±SEM. The results are representative of 4 independent experiments.

FIG. 17 demonstrates that an active form of GFP, expressed within the alga vacuole, is absorbed from the fish intestine into its blood in an intact and functional form. Tilapia fish were force fed with vacuole-GFP expressing algae (construct 527) or with vacuole-fGH expressing algae (construct 398). Level of GFP in the blood was determined using fluorescence plate reader (515 nm). Results are shown as mean±SD. The results are representative of 3 independent experiments.

FIG. 18A shows the initial GFP-fluoresces obtained from vacuole-targeted GFP expressing algae (construct 527); total protein extract of these algae (GFP) and from vacuole-targeted fGH expressing algae (construct 398). FIG. 18B shows the fluorescence obtained from blood samples of Tilapia fish fed with each of the above-described algae or protein extract. Level of GFP in the blood was determined using fluorescence plate reader (515 nm). Results are shown as mean±SD.

DETAILED DESCRIPTION OF THE INVENTION

Figures 1, 2:
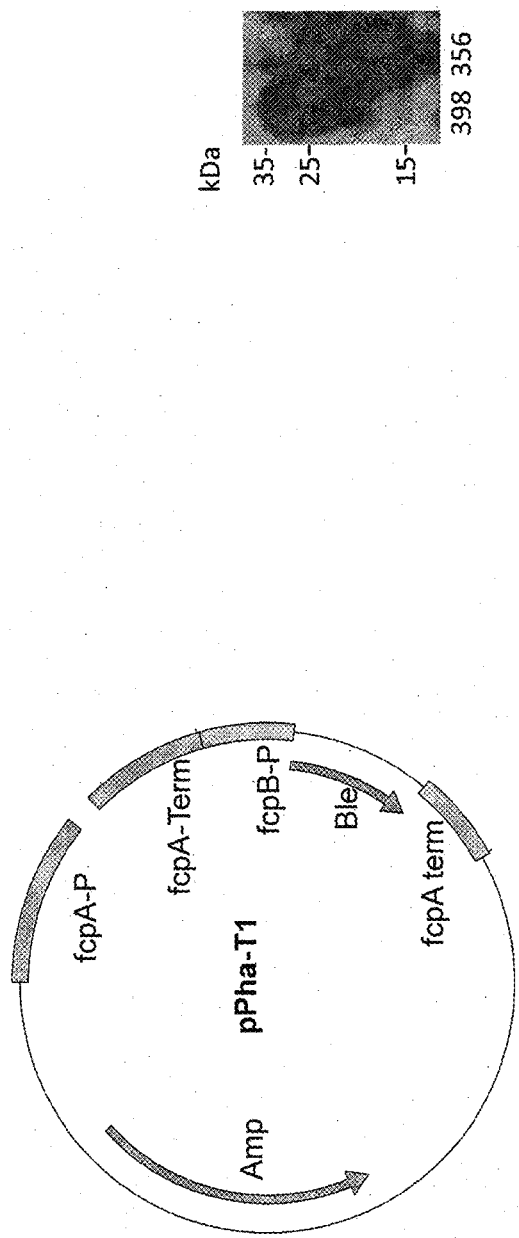
FIG. 1 shows a scheme of the complete pPhaT1 expression vector.
FIG. 2 shows Western blot of proteins extracted from transgenic algae of the species *Phaeodactylum tricornutum* expressing Salmon growth hormone targeted to different sub-cellular organelles.

The present invention provides compositions and methods for oral delivery of biologically active proteins to an organism in need of such proteins. Particularly, the present invention provides microalgae expressing the biologically active protein and edible compositions comprising same. The present invention demonstrates that the biological activity of the protein is maintained within the consumed algae and furthermore, that the protein exerts its biological activity in cells or tissues of the organism consuming the transgenic microalgae.

Definitions

The terms "microalga" or "microalgae" is used herein in its broadest scope and refer to unicellular microscopic eukaryotic algae, typically found in freshwater and marine systems. Depending on the species, the microalgae size can range from a few micrometers (µm) to a few hundreds of micrometers. According to certain currently specific embodiments, the term refers to marine eukaryotic microalga or microalgae.

The term "gene" refers to a nucleic acid (e.g., DNA or RNA) sequence that comprises coding sequences necessary for the production of RNA or a polypeptide. A polypeptide can be encoded by a full-length coding sequence or by any part thereof. The term "parts thereof" when used in reference to a gene refers to fragments of that gene. The fragments may range in size from a few nucleotides to the entire gene sequence minus one nucleotide. Thus, "a nucleic acid sequence comprising at least a part of a gene" may comprise fragments of the gene or the entire gene.

The term "gene" optionally also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The terms "protein", "protein sequence" and amino acid sequence" are used interchangeably throughout the specification to designate a linear series of amino acid residues connected one to the other by peptide bonds. The term also encompasses peptides.

The terms "polynucleotide", "polynucleotide sequence" and "nucleic acid sequence" are used interchangeably herein. These terms encompass nucleotide sequences and the like. A polynucleotide may be a polymer of RNA or DNA or hybrid thereof, that is single- or double-stranded, linear or branched, and that optionally contains synthetic, non-natural or altered nucleotide bases. The terms also encompass RNA/DNA hybrids. According to certain currently exemplary embodiments, the polynucleotides of the present invention are designed based on the amino acid sequence of the protein of interest employing a codon usage of the particular microalga species to be transformed.

The terms "expression cassette" and "construct" or "DNA construct" are used herein interchangeably and refer to an artificially assembled or isolated nucleic acid molecule which includes the polynucleotide encoding the protein of interest. The construct may further include a marker gene which in some cases can also encode a protein of interest. The expression cassette further comprising appropriate regulatory sequences operably linked to the polynucleotide encoding the protein of interest. It should be appreciated that the inclusion of regulatory sequences in a construct is optional, for example, such sequences may not be required in situations where the regulatory sequences of a host cell are to be used.

According to certain embodiments, the organism comprises an expression cassette comprising operably linked a promoter sequence, a polynucleotide encoding the protein of interest and a termination sequence.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The terms "promoter element," "promoter," or "promoter sequence" as used herein, refer to a DNA sequence that is located upstream to the 5' end (i.e. proceeds) the protein coding region of a DNA polymer. The location of most promoters known in nature precedes the transcribed region. The promoter functions as a switch, activating the expression of a gene or part thereof. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. Promoters may be derived in their entirety from a native gene, or be composed of different elements derived from different promoters found in nature, or even comprise synthetic DNA segments. It is understood by those skilled in the art that different promoters may direct the expression of a gene or part thereof in different tissues or cell types, or at different stages of development, or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters".

According to the teachings of the present invention, the promoter can be the organism's native promoter or a heterologous promoter, which may be a constitutive promoter, an induced promoter or a tissue specific promoter.

Any promoter known in the art to be active in microalgae can be used according to the teachings of the present invention. Non-limiting examples are fucoxanthin chlorophyll protein A (fcpA); B (fcpB); C (fcpC) and E (fcpE) promoters as well as any light harvesting complex (Lhc) promoter. Non-light harvesting related promoters can also be used, including, but not limited to, the nopaline synthase promoter; poly-adenylation sequences from the Ti plasmid of *Agrobacterium tumefaciens*; the promoter region of the tubB2; the PL promoter from bacteriophage λ; the CaMV 35S promoter; the bacterial tφ promoter; the heat shock protein 70A promoter (HSP70A); and a promoter of Rubisco small subunit 2 (RBCS2).

As used herein, the term "food" refers to food for human or animal consumption, including land and aquatic animal.

The term "aquaculture" as used herein refers to aquatic organism cultivated under controlled conditions. An "aquatic organism" is an organism grown in water, either fresh- or saltwater. Aquatic organisms, include, but are not limited to, fish, e.g., bass, striped bass, tilapia, catfish, sea bream, rainbow trout, zebra fish, red drum, goldfish, *Koi* fish, Angel fish and carp; crustaceans, e.g., penaeid shrimp, brine shrimp, freshwater and saltwater shrimp, and *Artemia*; and rotifers.

Specific Embodiments for Carrying Out the Invention

The teachings of the present invention are illustrated below with regard to animals, particularly animals grown in aquaculture and model land animals as non-limiting examples for implementation of at least some aspects of the present invention.

Currently available aquaculture systems are generally classified as open or closed. Open systems are typically created by building a net-pen in a body of water, such as a lake or stream. Closed systems generally recirculate the water in a closed tank, the water being pumped from the tank through a treatment cycle and back into the tank.

Aquaculture systems are used to grow aquatic animals such as fish, crustaceans and mollusks, to a size where they are marketable for different uses, primarily as food products but also as ornamentals. According to at least some embodiments the present invention provides improved food for fish or other aquatic animal. Suitable food forms an important aspect of aquaculture systems; the teachings of the present invention provide means and methods for producing food with enhanced outcome including improved growth (including enhancing the length and/or weight gain), improved growth pattern (particularly reducing or eliminating body deformation), shortening the time to sexual maturation or another life cycle stage, improved overall health (including increasing the survival rate) or combinations thereof.

Oral administration of an edible composition comprising a biologically active protein is of significant economical value in aquaculture as well as in agriculture, eliminating the need to administer the composition to each animal individually.

Therapeutic edible compositions are also highly desired for humans, as their administration does not require professional manpower (required for administration of a therapeutic compound e.g. intravenously) and are easy to consume thus enhancing the compliance of the patients in taking the prescribed dose.

According to one aspect, the present invention provides a transgenic eukaryotic microalga comprising an expression cassette comprising at least one transcribable polynucleotide encoding a biologically active exogenous protein, wherein the biologically active exogenous protein is expressed within a subcellular compartment of the microalga cell.

Various algae species can be used according to the teachings of the present invention. According to certain embodiments, the alga is marine microalga. An exemplary list of marine microalga that can be used according to the teachings of the present invention includes, but is not limited to, *Phaeodactylum tricornutum; Dunaliella* spp.; *Nannochloropsis* spp. including *Nannochloropsis oculata, Nannochloropsis salina, Nannochloropsis gaditana; Nannochloris* spp., *Tetraselmis* spp. including *Tetraselmis suecica, Tetraselmis chuii; Isochrysis galbana; Pavlova* spp.; *Amphiprora hyaline; Chaetoceros muelleri*; and *Neochloris oleoabundans*. The algae come from and represent a large taxonomical cross section of species (Table 1).

TABLE 1

Phylogeny of some of the eukaryotic algae

| Genus | Family | Order | Phylum | Kingdom |
|---|---|---|---|---|
| Phaeodactylum | Phaeodactylaceae | Naviculales | Bacillariophyta | Chromalveolata |
| Dunaliella | Dunaliellaceae | Chlamydomonadales | Chlorophyta | Viridaeplantae |
| Nannochloris | Coccomyxaceae | Chlorococcales | Chlorophyta | Viridaeplantae |
| Tetraselmis | Chlorodendraceae | Chlorodendrales | Chlorophyta | Viridaeplantae |
| Nannochloropsis | Monodopsidaceae | Eustigmatales | Heterokontophyta | Chromobiota |
| Pavlova | Pavlovaceae | Pavlovales | Haptophyta | Chromobiota |
| Isochrysis | Isochrysidaceae | Isochrysidales | Haptophyta | Chromobiota |

Phylogeny according to Guiry, M D and Guiry G M. 2013. AlgaeBase. World-wide electronic publication, National University of Ireland, Galway.

According to certain specific embodiments, the transgenic microalga used according to the teachings of the present invention is *Phaeodactylum tricornutum*. The alga *Phaeodactylum tricornutum* is a diatomaceous unicellular alga that forms part of phytoplankton and originates from temperate climes. This alga is readily amenable to transformation and the transformed alga growth well in aquaculture. In addition, this alga is nontoxic and nonpathogenic, and can be used as a food source for animals, especially fish and marine invertebrates but also for land animals.

The primary use of the transgenic microalgae of the present invention is as an edible composition. The exogenous protein expressed in the algal cell should reach the target cell or tissue of the subject consuming the composition in its active form, wherein the subject is aquatic or land animal, including humans. One of the principal obstacles in oral delivery of a biologically active protein is the susceptibility of the protein to the environmental conditions throughout the process of preparing the oral delivery product and its storage and thereafter within the body of the target subject in the gastrointestinal tract.

The present invention now shows that the exogenous protein expressed within a subcellular compartment of the microalga preserves its activity when consumed by aquatic as well as by terrestrial animals. Without wishing to be bound by any specific theory or mechanism of action, the protein activity may be preserved by the intact alga cell, particularly by the cell walls, which may act as a form of encapsulation that protect the protein from the outside harsh environment throughout the growth and processing of the algal biomass and furthermore from the environment of the gastrointestinal tract of the subject animal consuming the algae.

According to certain embodiments, the subcellular compartment is selected from the group consisting of vacuole, endoplasmic reticulum, *Golgi* system, lysosome and peroxisome. Each possibility represents a separate embodiment of the present invention. According to certain currently specific embodiments, the exogenous protein is expressed within the microalga cell vacuole. Expressing the exogenous protein within the alga chloroplast is explicitly excluded from the present invention.

Another problem to be solved in oral delivery of proteins is the penetration of proteins and peptides through the gastrointestinal epithelial cell membranes of the target animal subject that strictly limits their penetration. A minimum level of lipophilicity is needed for the proteins to partition into epithelial cell membranes for transcellular absorption. Unexpectedly, the present invention now shows that targeting the polynucleotides to be expressed within the plant vacuole lead to efficient transfer of the expressed, biologically active protein into the blood stream of the animal consuming the transgenic microalgae. Targeting the protein into the vacuole was advantageous over targeting to other cell compartments, including chloroplasts. Vacuoles are part of the endomembrane system of a cell; therefore, without wishing to be limited by a single hypothesis or mechanism of action, targeting peptides or proteins to the microalga cell vacuole, which is part of the endomembrane system, may increase absorption through the gastrointestinal tract of the animal once the alga is consumed and its walls are degraded by the animal subject. Such an increase in absorption may be due to increasing the "perceived" lipophilicity of peptide and protein molecules by the epithelial cell membranes, resulting in efficient absorption through the intestine. In addition, it is also possible that providing the protein through the vacuole increases storage stability of the protein. Various combinations of the above may also play a role. In any case, targeting the protein to the vacuole clearly increases the functional efficacy of orally administered proteins, as described an exemplified below in greater detail.

Additionally, exogenous protein expressed by the microalgae can be so designed to enhance its uptake by the epithelial cell membranes of the animal subject consuming the transgenic algae. According to some embodiments, the expression cassette of the present invention further comprises a polynucleotide encoding a protein domain that enhances the uptake of the expressed exogenous protein by a xenogeneic cell or tissue.

The particular uptake enhancing domain is selected according to the type of the xenogeneic cell, which depends on the species of the subject animal consuming the transgenic microalgae. According to certain embodiments, the expression cassette further comprises a polynucleotide encoding a cell penetrating peptide (CPP). According to some embodiments, the CPP is selected from the group consisting of, but not limited to, the trans-activating transcriptional activator (TAT) from Human Immunodeficiency virus 1 synthesized according to the *Phaeodactylum tricornutum* codon usage (SEQ ID NO:9) or part thereof; and the membrane translocating sequence (MTS) of a fibroblast growth factor synthesized according to the *Phaeodactylum tricornutum* codon usage (SEQ ID NO:7) or part thereof. Each possibility represents a separate embodiment of the present invention.

Proteins having various biological activities can be expressed in the microalga cell according to the teachings of the present invention. According to certain embodiments, the protein has a therapeutic effect on the subject consuming the transgenic microalga. According to other embodiments, the protein enhances the growth of the subject consuming the transgenic microalga. According to yet additional embodiments, the protein enhances the survival of the subject consuming the transgenic microalgae. According to yet additional embodiments, the protein enhances the reproduction rate of the subject consuming the transgenic microalgae.

According to certain exemplary embodiments, the transgenic microalga expresses a hormone. According to some embodiments, the hormone is selected from the group consisting of appetite inducing hormone, gonadotropin releasing hormone (spawning hormone) and a growth hormone. According to certain currently specific embodiments the growth hormone is fish growth hormone.

It is to be understood that the present invention excludes use of the transgenic microalgae of the present invention as a source of exogenous proteins for vaccines.

Any method for transforming microalgae as is known in the art can be used according to the teachings of the present invention. Transformation methods include particle bombardment, electroporation, microporation, vortexing cells in the presence of exogenous DNA, acid washed beads and polyethylene glycol-mediated transformation. Methods and tools for transformation of eukaryotic algae can be found, for example, in International (PCT) Application Publication No. WO 1997/039106.

Typically, to prepare vectors for making the transgenic algae, the polynucleotide encoding the exogenous protein is first cloned into an expression vector, a plasmid that can integrate into the algal genome. In such an expression vector, the DNA sequence which encodes the exogenous protein is operatively linked to an expression control sequence, i.e., a promoter, which directs mRNA synthesis. As described hereinabove, the promoter can be an endogenous promoter, i.e., a promoter that directs transcription of genes that are normally present in the algae. According to certain embodiments, the vector further comprises a polynucleotide encoding a resistance gene to enable selection of transformed algae. According to certain currently exemplary embodiments, the vector comprises a polynucleotide encoding a protein conferring resistance to zeocine and phleomycin.

Culturing conditions of the transformed algae depend on the alga species used, as is known to the skilled Artisan and as exemplified hereinbelow. Typically, the algae are grown under conditions that enable photosynthesis. Since photosynthesis requires sunlight and $CO_2$ and the microalgae further require either fresh, brackish or marine water mixed with the appropriate fertilizers to grow, microalgae can be cultivated in, for example, open ponds and lakes. However, the open systems are more vulnerable to contamination than a closed system, and furthermore, genetically modified microalgae grown in open aqueous reservoirs may be taken as hazardous to the environments. In addition, in open systems there is less control over water temperature, $CO_2$ concentration, and lighting conditions. The growing season is largely dependent on location and, aside from tropical areas, is limited to the warmer months of the year. An open system, however, is cheaper to set up and/or maintain than a closed system.

Another approach to growing the microalgae is thus to use a semi-closed system, such as covering the pond or pool with a structure, for example, a "greenhouse-type" structure. While this can result in a smaller system, it addresses many of the problems associated with an open system. The advantages of a semi-closed system are that it can allow for the desired microalgae to be dominant over an invading organism by allowing the microalgae of interest to out-compete the invading organism for nutrients required for its growth, and it can extend the growing season. For example, if the system is heated or cooled, the microalgae can grow year round.

Alternatively, the microalgae can be grown in closed structures such asphotobioreactors, where the environment is under stricter control than in open systems or semiclosed systems. A photobioreactor is a bioreactor which incorporates some type of light source to provide photonic energy input into the reactor. The term photobioreactor can refer to a system closed to the environment and having no direct exchange of gases and contaminants with the environment. A photobioreactor can be described as an enclosed, illuminated culture vessel designed for controlled biomass production of phototrophic liquid cell suspension cultures. Examples of photobioreactors include, for example, glass containers, plastic/glass tubes, tanks, plastic sleeves, and bags. Examples of light sources that can be used to provide the energy required to sustain photosynthesis include, for example, fluorescent bulbs, LEDs, and natural sunlight. Because these systems are closed everything that the organism needs to grow (for example, carbon dioxide, nutrients, water, and light) must be introduced into the bioreactor. Photobioreactors, despite the costs to set up and maintain them, have several advantages over open systems, they can, for example, prevent or minimize contamination, offer better control over the culture conditions (for example, pH, light, carbondioxide, and temperature), prevent water evaporation, lower carbon dioxide losses due to degassing, and permit higher cell concentrations. On the other hand, certain requirements of photobioreactors, such as cooling, mixing, control of oxygen accumulation and bio-fouling, make these systems more expensive to build and operate than open systems or semi-closed systems. Photobioreactors can be set up to be continually harvested (as is with the majority of the larger volume cultivation systems), or harvested one batch at a time (for example, as with polyethlyene bag cultivation). A batch photobioreactor is set up with, for example, nutrients, microalgae, and water, and the microalgae is allowed to grow until the batch is harvested. A continuous photobioreactor can be harvested, for example, either continually, daily, or at fixed time intervals.

$CO_2$ can be delivered to any of the systems described herein, for example, by bubbling in $CO_2$ from under the surface of the liquid containing the microalgae. Also, sparges can be used to inject $CO_2$ into the liquid. Spargers are, for example, porous disc or tube assemblies that are also referred to as Bubblers, Carbonators, Aerators, Porous Stones and Diffusers.

Nutrients that can be used in the systems described herein include, for example, nitrogen (in the form of $NO_3^-$ or $NH_4$, phosphorus, and trace metals (Fe, Mg, K, Ca, Co, Cu, Mn, Mo, Zn, V, and B). The nutrients can come, for example, in a solid form or in a liquid form. If the nutrients are in a solid form they can be mixed with, for example, fresh or salt water prior to being delivered to the liquid containing the microalgae, or prior to being delivered to a photobioreactor.

The microalgae can be grown in large scale cultures, where large scale cultures refers to growth of cultures in volumes of greater than about 6 liters, or greater than about 10 liters, or greater than about 20 liters. Large scale growth can also be growth of cultures in volumes of 50 liters or more, 100 liters or more, or 200 liters and up.

Optimal growth temperature is typically about 20° C. to about 25° C., however it is species dependent. According to certain embodiments microalgae cell reach a density of $10^5$ to $10^5$/ml before harvesting.

Post-harvest processing of some sort may be used to prepare the material for oral consumption or as a food composition. Conventional processes typically include at least partial separation of the algal biomass from the liquid culture in which the algae were grown. Optionally, the algal biomass can be homogenized and/or dried to form pellets of various sizes, depending on the target subject and mode of application. Other modes of preparation include spray drying, fluid bed drying, or even providing the material as a liquid suspension.

The harvested transgenic microalgae of the present invention can be administered per se, can be formulated into an edible composition further comprising edible diluents, excipients or carriers. The microalgae or the composition comprising same can be further used as food additive. According to some embodiments, the edible composition is an animal food composition. According to certain currently specific embodiments, the animal food composition if for feeding aquatic and land animals. According to yet other embodiments, the edible composition is for human consumption.

According to a further aspect the present invention provides a method for improving at least one of an animal growth rate, growth pattern, reproductive health status, survival or any combination thereof, comprising administering to the animal transgenic microalgae of the present invention or a composition comprising same, thereby improving the growth rate and/or the growth pattern and/or the survival and/or the reproductive health status of said animal.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

These Examples relate to specific implementations of at least some aspects of embodiments of the present invention. The Examples are illustrative only and are not intended to be limiting in any way.
Materials & Methods
Synthesis of Salmon Growth Hormone Gene The amino acid sequence of the Salmon growth hormone (accession No. AAT02409) was used as the basis for the synthesis of a polynucleotide encoding a mature Salmon growth hormone (SEQ ID NO:12, designated herein "fish growth hormone" or "fGH"). The polynucleotide synthesis was performed using the *Phaeodactylum tricornutum* codon usage of "Entelechon GmbH", thereby forming a novel polynucleotide sequence shown in SEQ ID NO:1. This novel sequence was not previously disclosed, as this codon usage has not yet been used for this protein. Furthermore, this specific sequence was designed to be more efficiently expressed by *Phaeodactylum tricornutum*, as discussed in greater detail below.
Construction of the Salmon Growth Hormone Gene Targeted to ER The fGH growth hormone gene was fused at its 5' end to a polynucleotide encoding Bip endoplasmic reticulum leader sequence (Kilian O and Kroth P. 2005. The Plant Journal: 41:175-183) (nucleic acids: SEQ ID NO:16; amino acids: SEQ ID NO:2) to produce the Bip-fGH (nucleic acids: SEQ ID NO: 17; amino acids: SEQ ID NO:3), according to the following:

The Bip leader sequence was amplified from *Phaeodactylum tricornutum* genomic DNA using the following primers:

```
                                       (SEQ ID NO: 36)
Forward BiP:         GGAATTCATGATGTTCATGAGAATTGC (SEQ ID NO: 37)
Reverse Bip-fGH-V2   ACGCTGGTTTTCAATCACGGTACCCATCTT.
```

The Bip leader sequence product was amplified using the following primers:

```
                                       (SEQ ID NO: 38)
Forward BiP          GGAATTCATGATGTTCATGAGAATTGC.

(SEQ ID NO: 39)
Reverse Bip-fGH-V2   ACGCTGGTTTTCAATCACGGTACCCATCTT.
```

The fGH was amplified using the following primers:

```
                                       (SEQ ID NO: 40)
Forward Bip-fGH-V2   AAGATGGGTACCGTGATTGAAAACCAGCGT.

(SEQ ID NO: 41)
Reverse fGH BglII    GAGATCTGAGGGTGCAGTTGG.
```

The Bip leader sequence was fused to fGH by a third PCR, using the amplified PCR products (Bip, fGH), and the mentioned primers for Bip+Revf BgIII, resulting in the construct designated 356 having the nucleic acid sequence set forth in SEQ ID NO:17 and the amino acid sequence set forth in SEQ ID NO:3.
Construction of the Salmon Growth Hormone Gene Targeted to Vacuole The fGH encoding polynucleotide was fused to a vacuole leader sequence (nucleic acids: SEQ ID NO:18; amino acids: SEQ ID NO:4) at its 5' and to an HA tag (nucleic acids: SEQ ID NO:47; amino acids: SEQ ID NO:5) at its 3' to produce the vacuole-fGH-HA polynucleotide (nucleic acids: SEQ ID NO:19; amino acids: SEQ ID NO:6), according to the following:

The synthetic fGH was amplified using the following primers:

```
                                       (SEQ ID NO: 42)
Forward fGH EcoRI  GGAATTCATGGGCCAAGTCTTTCTCTTG (SEQ ID NO: 41)
Reverse fGH BglII  GAGATCTGAGGGTGCAGTTGG.
```

The product was ligated to a pPhaT1-HA plasmid using EcoRI, BgIII.

The fGH-HA template was amplified using the following primers:

```
Forward fGH BamHI:
                                       (SEQ ID NO: 43)
GGATCCATTGAAAACCAGCGTTTGTTCAAC.

Reverse Hind HA:
                                       (SEQ ID NO: 44)
AAGCTTTTACTGGGCGGCGTAGTCCGGGACGTCGTAGGGGTA.
```

The PCR product was cloned into pPhaT1 by BamHI and HindIII.

The vacuole leader sequence was amplified from *Phaeodactylum tricornutum* cDNA using the following primers:

```
                            (SEQ ID NO: 45)
EcoR1-Vac54681:  ATGAATTCATGTCGATTCGTCTCT.

(SEQ ID NO: 46)
BamH1-Vac54681:  ATGGATCCAGTTTGGGCAGTTGCC.
```

The fGH-HA and the vacuole leader sequence were ligated with EcoRI and BamHI, resulting in the construct designated 398, having the nucleic acid sequence set forth in SEQ ID NO: 19 encoding the polypeptide having the amino acids sequence set forth in SEQ ID NO:6.

Construction of the GFP-Encoding Polynucleotide Targeted to Vacuole

In the construct described above, the polynucleotide encoding the fish growth hormone was replaced with a polynucleotide encoding GFP (accession P42212, having the nucleic acid sequence set forth in SEQ ID NO:29 and encoding a protein having the amino acid sequence set forth in SEQ ID NO:28) by BamHI and HindIII, leading to a vacuole targeted GFP (SEQ ID NO:30, amino acid sequence; SEQ ID NO:31, nucleic acid sequence—prepared with *Phaeodactylum tricornutum* codon usage), resulting in a construct designated 527, having the nucleic acid sequence set forth in SEQ ID NO:31 and the amino acid sequence set forth in SEQ ID NO:30.

Construction of the Vacuole-fGH-MTS-HA

A membrane translocating sequence (MTS) from the fibroblast growth factor was synthesized according to the *Phaeodactylum tricornutum* codon usage by Biomatik (SEQ ID NO:7). The translocating sequence was ligated to the vacuole-fGH-HA at the 3' of fGH using BglII, to produce the construct encoding vacuole-fGH-MTS-HA having the amino acid sequence set forth in SEQ ID NO:8.

Construction of the Vacuole-GFP-MTS

A membrane translocating sequence (MTS) from the fibroblast growth factor was synthesized according to the *Phaeodactylum tricornutum* codon usage by Biomatik. The translocating sequence was ligated to the vacuole-GFP at the 3' of GFP using HindIII, to produce the vacuole-GFP-MTS construct (nucleic acid sequence: SEQ ID NO:33; amino acid sequence SEQ ID NO: 32).

Construction of the Vacuole-fGH-TAT-HA

A trans-activating transcriptional activator (TAT) from Human Immunodeficiency virus 1 (HIV-1) was synthesized according to the *Phaeodactylum tricornutum* codon usage by Biomatik (SEQ ID NO:9). The domain was fused by BglII in tandem of two repeats to the vacuole-fGH-HA at the 3' of fGH to produce the vacuole-fGH-TAT-HA construct (SEQ ID NO:10).

Construction of the Vacuole-GFP-TAT

A trans-activating transcriptional activator (TAT) from Human Immunodeficiency virus 1 (HIV-1) was synthesized according to the *Phaeodactylum tricornutum* codon usage by Biomatik. The gene was ligated to the vacuole-GFP at the 3' of GFP using HindIII, to produce the vacuole-GFP-TAT construct having the nucleic acid sequence set forth in SEQ ID NO:35, encoding the vacuole-GFP-TAT protein having the amino acid sequence set forth in SEQ ID NO:34.

Cloning Constructs into an Algae Expression Vector

The various polynucleotides and constructs of the invention were further cloned under the control of the fcpA promoter and fcpA terminator in the plasmid pPHAT1 (accession number AF219942) (SEQ ID NO:11) according to Apt et al. (1996. Mol. Gen Genet. 252:572-579). The fcpA promoter is the only one that is currently known to be operative in *Phaeodactylum tricornutum*. However, it is to be explicitly understood that other promoters can be used in *Phaeodactylum tricornutum* as well as in other algae.

The vector contained:

An fcpA (fucoxanthin chlorophyll protein A) promoter, under which the gene of interest is cloned.

MCP—Multiple cloning site

An fcpB (fucoxanthin chlorophyll protein B) promoter, which controls the sh ble gene from *Streptoalloteichus hindustanus*, which encodes a protein that confers zeocine and phleomycin resistance.

fcpA terminators, which appear after the gene of interest and after the zeocine resistance gene.

Ampicillin resistant gene

Origin of replication from *Escherichia coli*.

FIG. 1 shows the complete pPhaT1 expression vector.

The fGH encoding polynucleotide (SEQ ID NO:1) was cloned under the fcpA promoter and fcpA terminator. The plasmid contained the selectable marker, Bleomycine, under the control of the fcpB promoter and fcpA terminator.

Cloning and Molecular Techniques

PCR reactions were done using Phusion Polymerase Cat. # FZ-F-5305 Finnzymes (Zotal) or REDTaq ready mix PCR reaction mix Cat. # R2523-100RXN Sigma. PCR reactions were cleaned using Wizard® SV Gel and PCR Clean-Up System (Cat. No. A9281, Promega).

Ligations were performed using DNA Ligation Kit (Mighty Mix)-Takara Cat. No. 6023 (Ornat) or T4 DNA ligase M0202T NEB (Eldan). Blunting of 5' or 3' overhangs was performed with $T_4$ DNA polymerase: (Fermentas #EP0061).

DNA Midi preps were performed using Pure Yield™ Plasmid Midiprep System A2492. PROMEGA and DNA minipreps were performed using AccuPrep Plasmid Mini Extraction Kit-BIONEER K-3030. DNA genomic isolations were performed according to Fawley & Fawley (Fawley M W and Fawley K P. 2004. J Phycol 40: 223-225). All kits and enzymes were treated according to the manufacturer's instructions.

Algae Culturing and Harvesting

Algae culturing and harvesting was done as described in U.S. Patent Application Publication No. 2011/0081706 to the Applicant of the present invention. Briefly, algae were cultured in filtered sea water enriched with F/2 nutrient for growing diatoms (modified from Andersen R et al. 2005. Recipes for freshwater and seawater media. In: Algal Culturing Techniques (R. A. Andersen, eds), pp. 429-538. Elsevier, Amsterdam). F/2 was added every 72 h at a dosage of 1:1000 to the final culture volume. A constant temperature regime was maintained at 21° C. Light: dark was set at 16:8 hours at a light intensity of 100 μmol photons per $m^2s^1$. $CO_2$ was mixed with air and delivered to the cultures at controlled ratio via the aeration systems. Algae were harvested for experiment near their maximal culture densities. To help flocculation of the algae calcium hydroxide was added to the culture as a fine suspension of particles in water containing 0.15 g/ml $Ca(OH)_2$, and the culture was then filtered or centrifuged. The resulting algae sediment was lyophilized.

Algae Transformation

I. Transformation by Particle Bombardment

Fresh algal culture were grown to mid exponential phase (2-5*$10^6$ cells/ml) in artificial sea water (ASW) F/2 media as described above. 24 hours prior to bombardment cells were harvested, washed twice with fresh ASW+F/2 and resuspended in 1/10 of the original cell volume in ASW+F/2. 0.5 ml of the cell suspension is spotted onto the center of a 55 mm Petri dish containing solidified ASW+F/2 media. Plates are left to dry under normal growth conditions. Bombardment was carried out using a PDS 1000/He biolistic transformation system according to the manufacturer's instructions (BioRad Laboratories Inc., Hercules, Calif. USA) using M17 tungsten powder (BioRad Laboratories Inc.) for cells larger than 2 microns in diameter, and tungsten powder comprised of particles smaller than 0.6 microns (FW06, Canada Fujian Jinxin Powder Metallurgy Co., Markham, ON, Canada) for smaller cells. The tungsten was coated with linear DNA. 1100 or 1350 psi rupture discs were used. All disposables were purchased from BioRad Laboratories Inc. After bombardment the plates were incubated under normal growth conditions for 24 hours after which the cells were plated onto selective solid media and incubated under normal growth conditions until single colonies appeared.

II. Transformation by Electroporation

Algal cultures were grown to mid exponential phase in artificial seawater (ASW)+F/2 media as described above. Cells were then harvested and washed twice with fresh media. After re-suspending the cells in 1/50 of the original volume, protoplasts were prepared by adding an equal volume of 4% hemicellulase (Sigma) and 2% Driselase (Sigma) in ASW and were incubated at 37° C. for 4 hours. Protoplast formation was tested by Calcofluor white non-staining. Protoplasts were washed twice with ASW containing 0.6M D-mannitol and 0.6M D-sorbital and resuspended in the same media, after which DNA was added (10 µg linear DNA for each 100 µl protoplasts). Protoplasts were transferred to cold electroporation cuvettes and incubated on ice for 7 minutes, then pulsed in an ECM830 electroporation apparatus (BTX, Harvard Apparatus, Holliston, Mass., USA). A variety of pulses is usually applied, ranging from 1000 to 1500 volts, 10-20 msec per pulse. Each cuvette was pulsed 5-10 times. Immediately after pulsing the cuvettes were placed on ice for 5 minutes and then the protoplasts were added to 250 µl of fresh growth media (non-selective). After incubating the protoplasts for 24 hours in low light at 25° C. the cells were plated onto selective solid media and incubated under normal growth conditions until single colonies appeared.

III. Transformation by Microporation

A fresh algal culture was grown to mid exponential phase in ASW+F/2 media. A 10 ml sample of the culture was harvested, washed twice with Dulbecco's phosphate buffered saline (DPBS, Gibco, Invitrogen, Carslbad, Calif., USA) and resuspended in 250 µl of buffer R (supplied by Digital Bio, NanoEnTek Inc., Seoul, Korea, the producer of the microporation apparatus and kit). After adding 8 µg linear DNA to every 100 µl cells, the cells were pulsed. A variety of pulses is typically needed, depending on the type of cells, ranging from 700 to 1700 volts, 10-40 msec pulse length; each sample was pulsed 1-5 times. Immediately after pulsing, the cells were transferred to 200 µl fresh culture media (non-selective). After incubating for 24 hours in low light at 25° C., the cells were plated onto selective solid media and incubated under normal culture conditions until single colonies appeared.

Protein Extraction 10 ml cells at $5 \times 10^6$ cell/ml were harvested and resuspended in 500 µl extraction buffer (50 mM Tris pH=7.0; 1 mM EDTA; 100 mM NaCl; 0.5% NP-40; and protease inhibitor (Sigma cat # P9599). Then 100 µl of glass beads (425-600µττκ, Sigma) were added and cells were broken in a bead beater (MP FastPrep-24, MP Biomedicals, Solon, Ohio, USA) for 20 sec. The tube content was centrifuged for 15 min, 13000×g, at 4° C. The supernatant was removed to new vial for quantification and Western blot analysis.

Protein Separation by SDS-PAGE and Western Analysis

Extracted proteins were separated on a 4-20% gradient SDS-PAGE (Geba gels 4-20% Bio-lab, 10GG0420-8), at 100V for 1 h. Following incubation of 1 h in blocking buffer (5% skim milk, Difco), proteins were either stained by Coomassie (Sigma) or blotted onto PVDF (Millipore, Billerica, Mass., USA) membranes for 1 h at 100 volts in transfer buffer (25 mM Tris, 192 mM glycine and 20% methanol). The proteins were detected either with an anti HA (Biotest MMS-101P-500) or the salmon growth hormone (GroPep: PAN1) antibodies, diluted to a ratio of 1:1000 in the blocking buffer. Mouse (for the HA antibody) or rabbit (for the Salmon growth hormone) horseradish peroxidases secondary antibodies (Millipore, Billerica, Mass., USA), at 1:10000 dilution in the blocking buffer were used. Detection was carried out using the EZ-ECL kit (Bio Ind. Promega: 20-500-120) according to manufacture instructions.

ELISA Analysis

ELISA plate (microlon, Greiner) was coated in carbonate/bicarbonate pH 9.6 with monoclonal anti HA Antibody (Sigma Aldrich) overnight at 4° C. Next, the plate was washed with PBST (0.05% Tween), and blocked with 1% BSA (Sigma Aldrich) in PBS for 4 hours at room temperature (RT). Serum samples were serially diluted in ELISA coating buffer and loaded onto the plate. After an overnight incubation with the serum samples, the plate was washed with PBST and incubated with anti HA-biotin (Roche) for 1 hour at room temperature. Following additional washing steps, horseradish peroxidase (HRP) conjugated sterptavidin was added and the plate was incubated for 1 hour at room temperature (RT). The plate was washed with PBST and tetramethyl-benzidine (TMB) substrate was added to the plate. Once sufficient color was developed, the reaction was stopped with 0.16M sulfuric acid. The absorbance in each well was measured at 450 nm using Enspire 2300 multilabel reader (PerkinElmer).

Fish Maintenance and Feeding

Groups of 10 Tilapia fish, weighing 70-100 grams were maintained in 100 liter aerated tanks at a temperature of 26-28° C. The photoperiod was 12 h light: 12 h dark. All fish were acclimated in the tanks for a week before the treatment. Oral administration with algae suspensions was conducted on fish lightly anesthetized with 100 ppm of clove bud extract (Roth). Polyethylene tube (length 6-8 cm, i.d. 3 mm) attached to an injecting syringe was used for oral administration (gavage feeding) of the different algal suspensions.

Feeding Trials

Lyophilized transgenic algae expressing the Salmon growth hormone were added in a final concentration of 1-4% to the regular fish feed. Fish received with feed at 10%-15% of their total body weight. The transgenic algae and the regular fish feed were used to feed the ornamental fish, *Koi, Scalare* and Goldfish *Shubunkin* for 6 weeks. Each trial was monitored for temperature, pH, ammonia, nitrite levels etc. At the end of each experiment fish total growth, morphological abnormalities and survival rates were analyzed.

Example 1: Algae Expressing Fish (Salmon) Growth Hormone

Transgenic algae of the species *Phaeodactylum tricornutum*, harboring the Salmon growth hormone encoding polynucleotide targeted to the ER (designated as construct 356) or to the vacuole (designated as construct 398) were cultured and analyzed for the expression of the transgenic protein. An equal amount of total soluble protein (20 "g) was extracted from the transgenic algae for Western blot analysis. Detection was made using anti Salmon growth hormone antibody as shown in FIG. 2.

The algae line expressing ER-targeted Salmon growth hormone has shown higher expression levels of the transgenic protein compared to the algae line expressing the vacuole-targeted growth hormone.

Example 2: Angel Fish Feeding Trial

Figure 3:
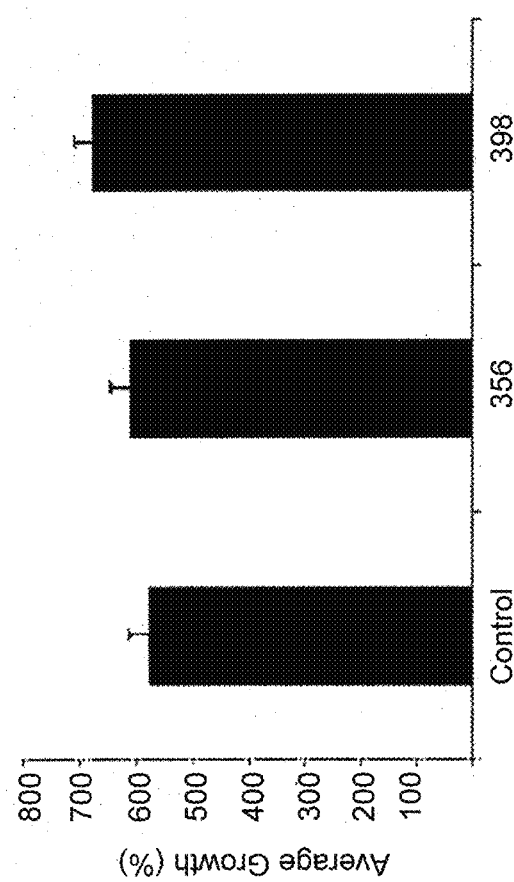
FIG. 3 shows the total growth performance of Angel fish fed with fish commercial regular food comprising transgenic algae overexpressing fish growth hormone (fGH) targeted to the ER (356) or to the vacuole (398), compared to fish fed with the regular fish food (control). Fish growth is presented as percentage of weight addition relative to the initial fish weight.

Ornamental Angel Fish (*Scalare*), were fed during 6 weeks with fish food supplemented with transgenic *Phaeodactylum tricornutum* over-expressing fish growth hormone targeted to the ER or to the vacuole (constructs 356, 398, respectively), or with the regular, non-transgenic fish food (control). The algae supplement was added at 4% into the regular fish food. Fish growth was followed within tanks as independent repeats (n=5) containing 20 fish each. FIG. 3 shows the total growth performance of the Angel fish treated with the transgenic algae (mixed within the fish food), compared to fish fed with regular fish food.

Fish fed with food containing the transgenic algae harboring construct 398 (in which the growth hormone was targeted to the vacuole) gave higher total fish biomass (~15%), compared to fish fed with the regular food (control), whereas fish fed with food containing the transgenic algae harboring construct 356 (in which the growth hormone was targeted to the ER) did not grow significantly better compared to the control.

Figure 4:
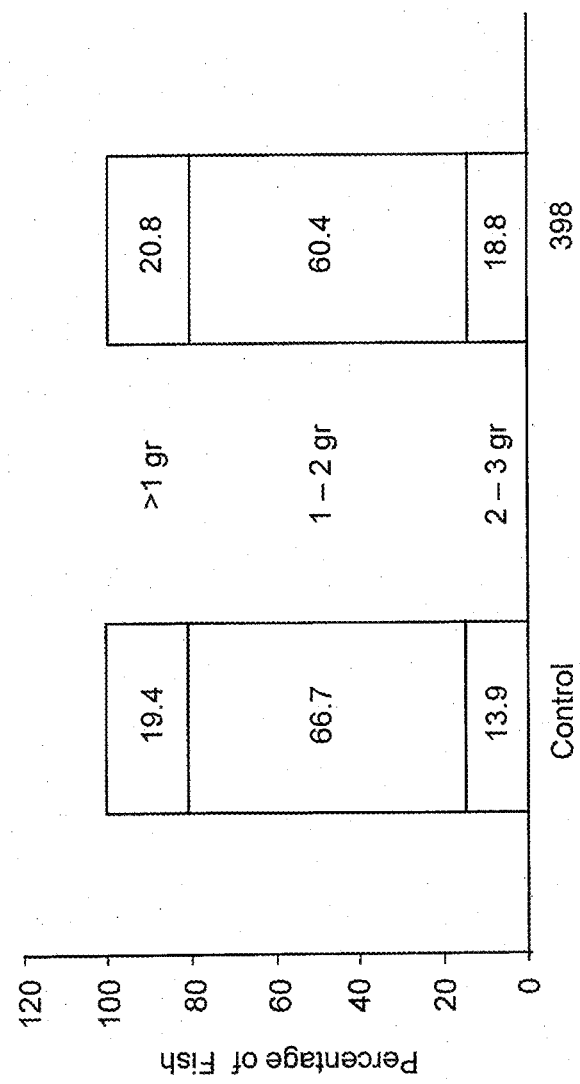
FIG. 4 shows that feeding fish with regular food containing vacuole targeted-fGH expressing algae (398) resulted in an increase in the number of fish reaching over 2 gr compared to fish fed with regular fish food.

In a parallel experiment, also conducted with Angel fish, feeding the fish with regular food containing algae expressing fGH targeted to the vacuole (construct 398) resulted in an increase in the number of fish reaching over 2 gr compared to fish fed with regular fish food (FIG. 4). From a marketing perspective this result implies that supplementation of regular fish food with algae expressing fGH targeted to the vacuole increases the number of fish which are suitable for marketing, without increasing the number of starting fish in the population or otherwise necessarily adjusting any aspect of the starting fish population.

Figure 5:
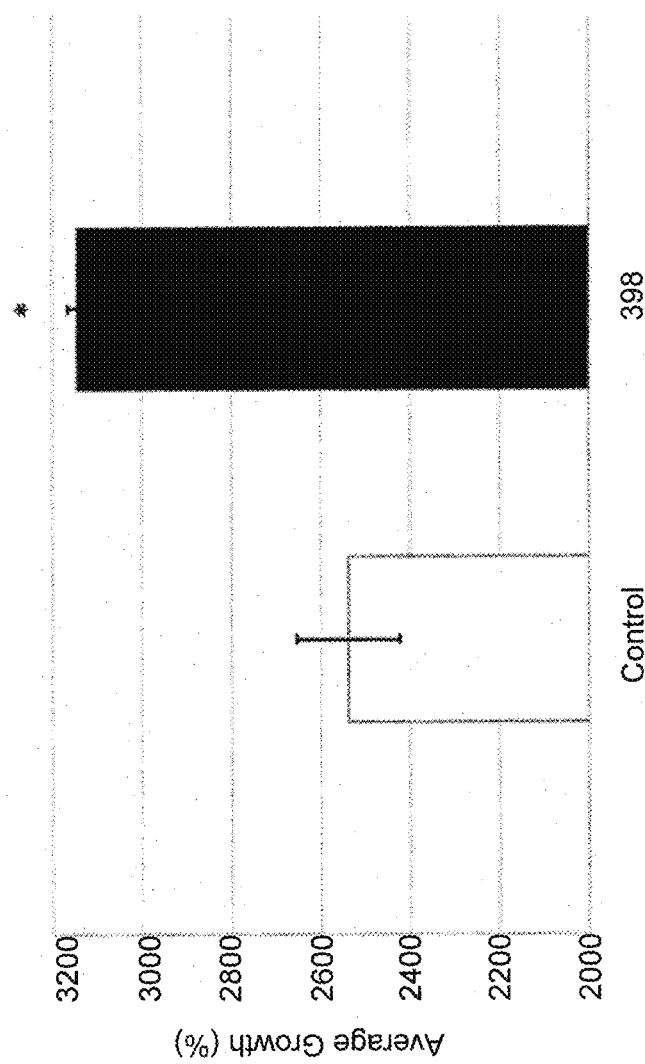
FIG. 5 shows the effect of transgenic algae overexpressing fGH administered as food supplement on the total weight of Angel fish. 398—Regular fish feed comprising 4% of vacuole targeted-fGH expressing algae. Control—regular fish feed only. Fish growth is presented as percentage of weight addition relative to the initial fish weight.

Another experiment conducted for 8 weeks with Angel fish in 5 repeats of 25 fish each, resulted in a significant biomass increase of fish consuming food supplemented with 4% algae expressing fGH (fGH expression targeted to the vacuole, construct 398) compared to fish fed with regular fish food (FIG. 5).

These results imply that the subcellular targeting of fGH to the vacuole of the alga cell results in better functional efficacy of the protein, even though the expression level was shown to be lower than the expression level of fGH targeted to cell ER.

Example 3: Koi Fish Feeding Trial

Figure 6:
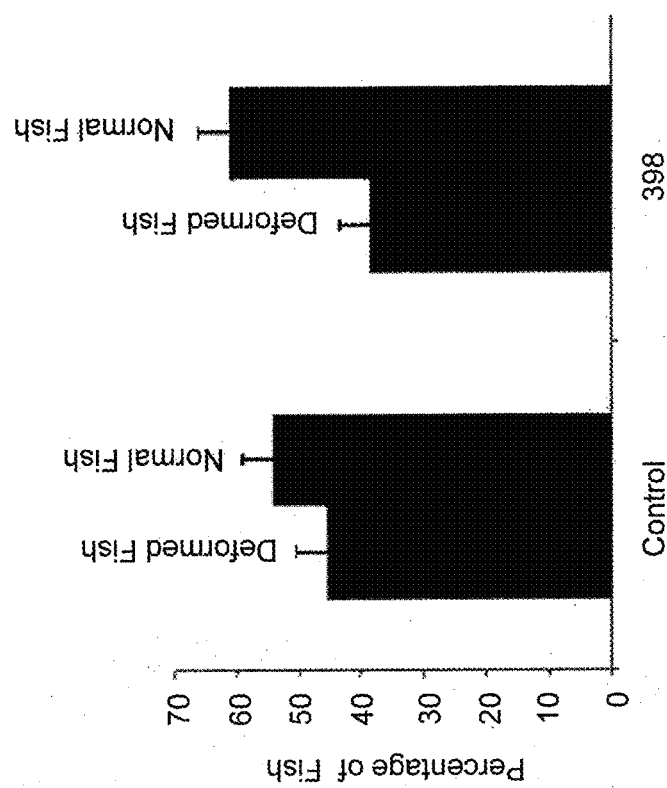
FIG. 6 shows the effect of consuming fish regular food comprising transgenic algae overexpressing vacuole targeted-fGH on deformations in shape of *koi* fish. 398—Regular fish food comprising 4% of fGH expressing algae. Control—regular fish food only.

Post larva *koi* fish (4 independent repeats each including 600 post larva *koi* fish) were fed either with the regular fish food or with regular fish food supplemented with 4% algae expressing fGH targeted to the vacuole (construct 398). The feeding experiment was performed over 8 weeks. At the end of the experiment, fish were screened for body deformation (as defined by Jha P et. al. 2006. Journal of Applied Ichthyology; 23 (1) 87-92). Body deformation includes but is not limited to any morphological irregularity, any type of body asymmetry, irregular body shape, irregular fin shape, irregular tail shape; irregular body/fin area, length or width ratios; irregular body/tail area, length or width ratios; irregular tail/fin area, length or width ratios; or irregularities in any body part. FIG. 6 shows the percentage of normal and deformed shape of fish fed with regular fish food and fish fed with regular food containing 4% of vacuole-targeted fGH expressing algae (construct 398).

As is apparent from FIG. 6, the population of fish receiving regular fish food exhibited 45% deformed fish, while the population of fish that received fish food supplemented with fGH expressing algae (construct 398) exhibited only 38% deformed fish.

Example 4: Goldfish Feeding Trial

Figure 7:
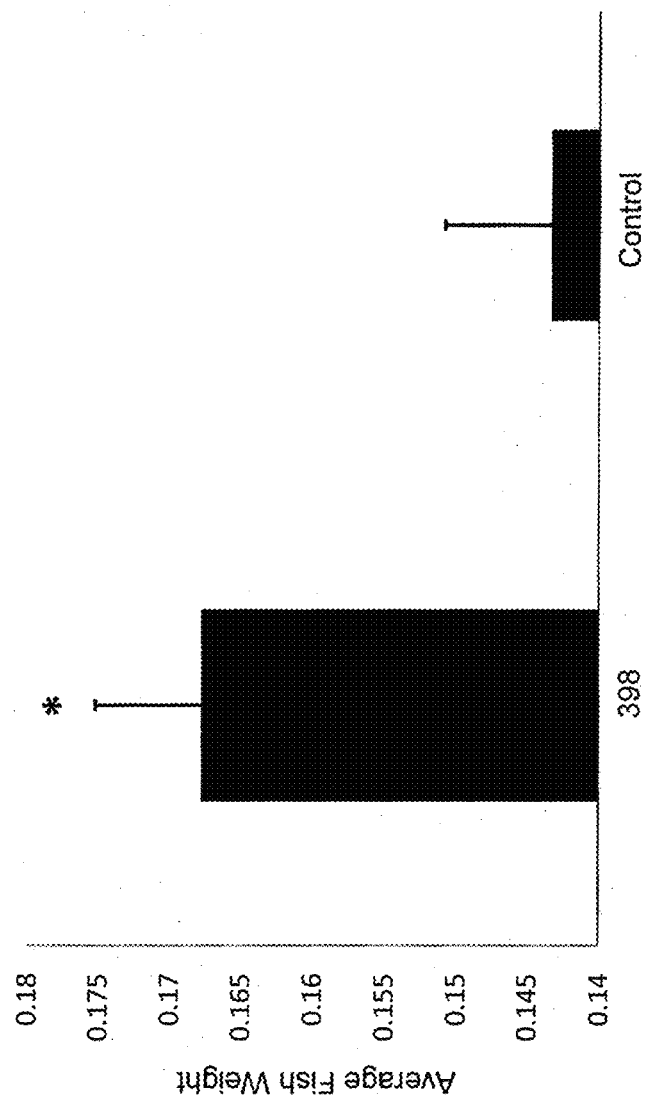
FIG. 7 shows the effect of consumption of transgenic algae overexpressing fGH on the total weight of goldfish. 398—Regular fish food comprising 4% of vacuole targeted-fGH expressing algae. Control—regular fish food only.

The post larva ornamental Goldfish (*Shubunkin*) were fed over 6 weeks with fish food supplemented with transgenic *Phaeodactylum tricornutum* overexpressing fish growth hormone targeted to the vacuole (construct 398), or with regular fish food (control). Algae supplement was added at 4% to the regular fish food. Treatments were tested in 6 independent repeats of 40 fish each. FIG. 7 shows that the total weight of goldfish fed with transgenic algae was higher by approximately ~15%, compared to fish fed with regular food.

In addition to the growth performance, the survival of fingerlings during the experiment was approximately 64% at the control tanks. The survival rate was elevated to approximately 80% within tanks in which the fish were fed with food supplemented with fGH expressing algae (construct 398), implying that the fGH expressing algae contributes to fish survival in addition to its growth enhancement effect.

Example 5: *Artemia* Feeding Trial

Figure 8A:
FIGS. 8A-8C show pictures of brine shrimp (*Artemia*) fed with wild type *Phaeodactylum tricornutum* (FIG. 8A), wild type *Nannochloris* (FIG. 8B) and *Phaeodactylum tricornutum* expressing vacuole targeted-fish growth hormone (FIG. 8C). Feeds were supplemented as live algae.
Figure 8B:
Figure 8C:
Figure 9:
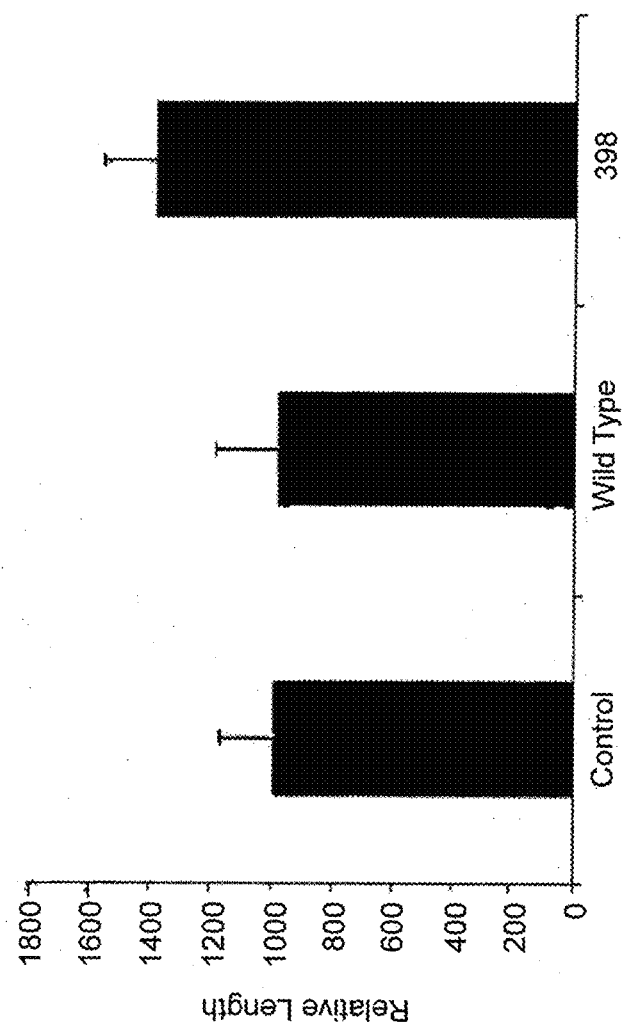
FIG. 9 shows the body length of Brine Shrimp fed with wild type *Nannochloris* (control); with wild type *Phaeodactylum tricornutum* (w.t.); or with *Phaeodactylum tricornutum* expressing fGH targeted to the vacuole (398). Feeds were supplemented as live algae.

Brine shrimps (*Artemia*) were fed for 12 days with wild type *Phaeodactylum tricornutum*, wild type *Nannochloris* or with fish growth hormone (fGH) expressing *Phaeodactylum tricornutum* (construct 398). *Artemia* fed with fGH expressing *Phaeodactylum tricornutum* were significantly larger (by about 40%) and the females reached sexual maturation 3 days earlier, when compared to *Artemia* fed with wild type *Nannochloris* or wild type *Phaeodactylum tricornutum* respectively (FIGS. 8 and 9).

Specifically, FIG. 8 shows the results after brine shrimp were fed with wild type *Phaeodactylum tricornutum* (FIG. 8A), wild type *Nannochloris* (FIG. 8B) or with *Phaeodactylum tricornutum* expressing fish growth hormone. Pictures were taken after 12 days.

FIG. 9 shows the measured average body length of fish receiving the different algae as the sole food. For the determination of body length, the body length of 26 randomly selected Brine Shrimp fed with wild type *Nannochloris* (control), Wild type *Phaeodactylum tricornutum* (wt) or fish growth hormone expressing *Phaeodactylum tricornutum* (construct 398) was measured after 12 days. Brine fish fed with fGH expressing algae were found to be significantly longer. Taken together, these results suggest that using algae expressing fish growth hormone targeted to the algal vacuole as food or food additive in Brine Shrimps and crustaceans enhance their growth, particularly with regard to body length, and sexual maturation.

Example 6: *Macrobrachium rosenbergii* Feeding Trial

The fresh water shrimp *Macrobrachium rosenbergii*, PL 10, were fed over 6 weeks with regular food (control), or with regular food supplemented with transgenic *Phaeodac-*

Figure 10:
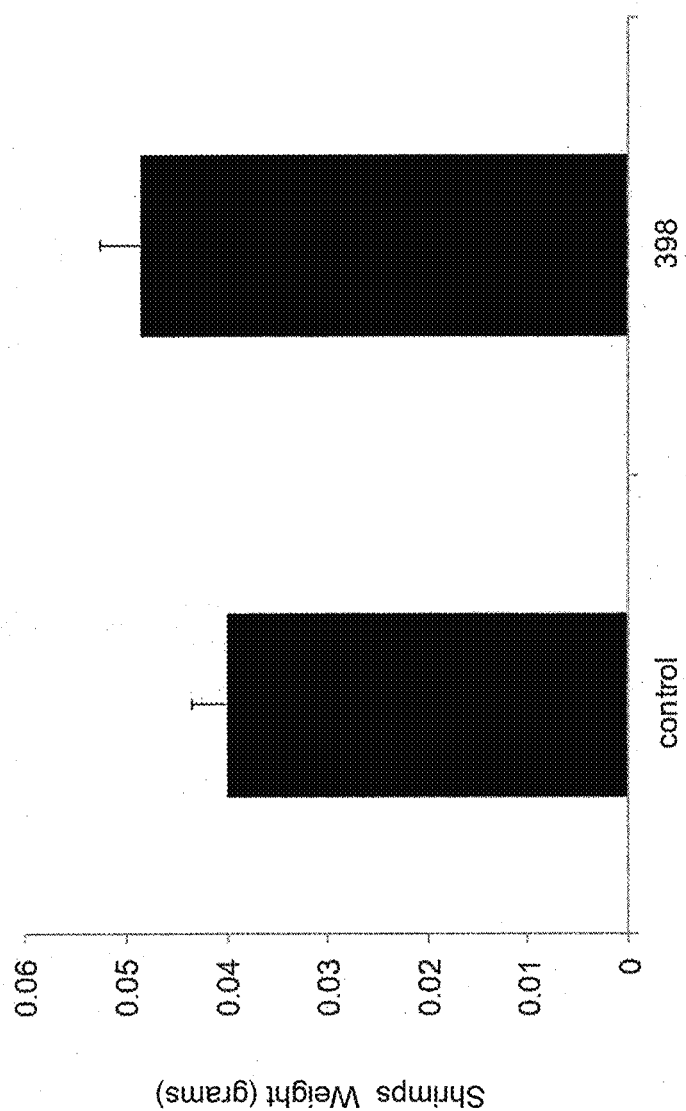
FIG. 10 shows the effect of food comprising microalgae expressing fGH on the weight of the shrimp *Macrobrachium rosenbergii*. 398—Shrimps fed with regular food supplemented with transgenic algae overexpressing fish growth hormone targeted to the algae vacuole. Control—shrimps fed with regular food only. Shrimp weight was measured after 6 weeks.

*tylum tricornutum* overexpressing fish growth hormone targeted to the algae vacuole (construct 398). Algae supplement was added at 8% to the regular food. FIG. 10 shows that the total weight of *Macrobrachium rosenbergii* treated with transgenic algae was significantly higher by 21%, compared to shrimps fed with regular food, implying that the fGH expressing algae contributes to the shrimp enhanced growth.

Figures 11A, 11B:
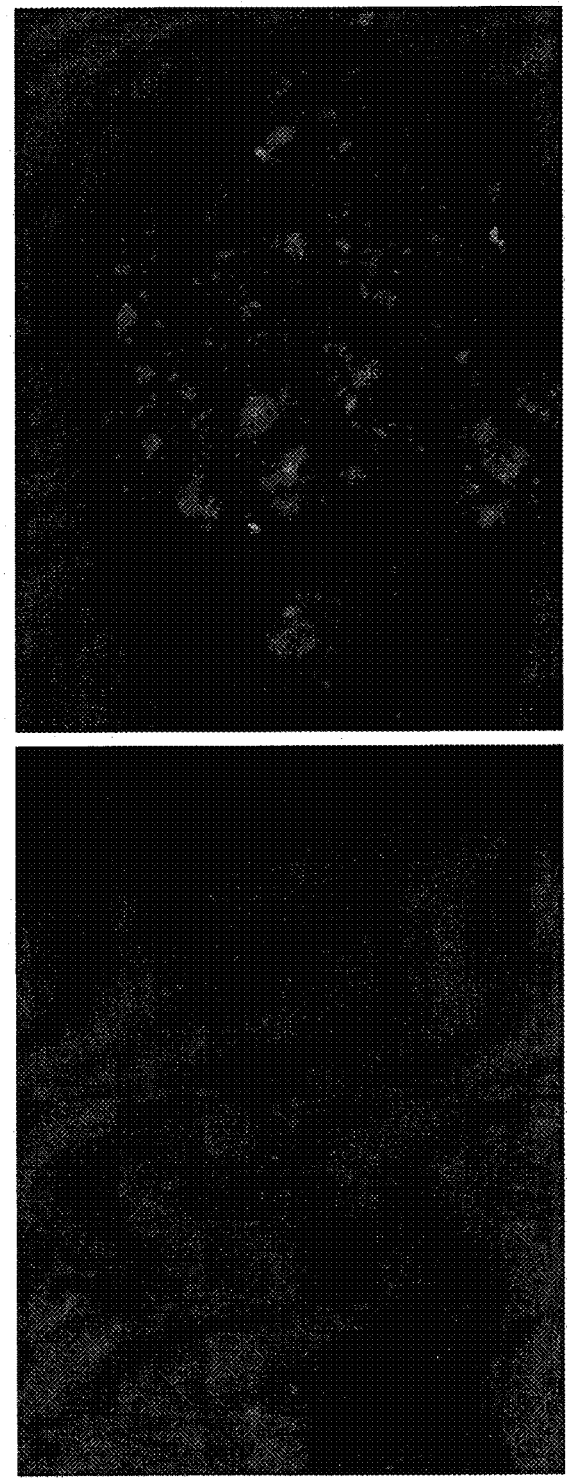
FIGS. 11A-11B show fluorescence imaging of stomachs of Tilapia fish fed with wild type algae (FIG. 11A) or with vacuole targeted—GFP expressing algae (construct 527, FIG. 11B). Pictures were taken 4 hours post feeding under fluorescent light.
Figure 12A:
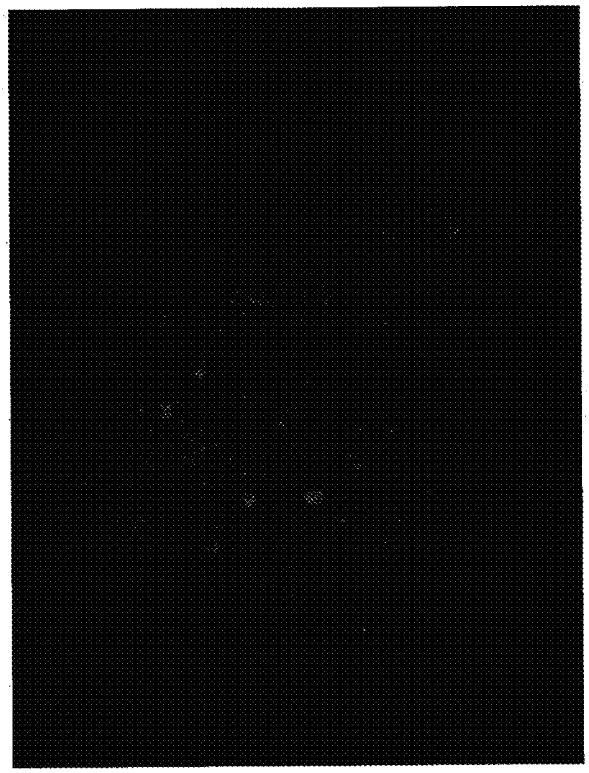
FIGS. 12A-12B show fluorescence imaging of intestines of Tilapia fish fed with wild type algae (FIG. 12A) or with vacuole-targeted GFP expressing algae (FIG. 12B). Pictures were taken 5 hours post feeding under fluorescent light.
Figure 12B:

Example 7: GFP Absorption by Fish 1 week starved Tilapia fish at a size of 50-100 grams were fed with fish food mixed with wild-type *Phaeodactylum tricornutum* or with *Phaeodactylum tricornutum* expressing GFP targeted to the vacuole at 1:1 fish food to algae ratio. Tilapia stomachs and intestines were taken out 1-4 hours post feeding and were analyzed under fluorescence binocular. FIG. 11 clearly shows fluorescence of the expressed exogenous GFP in the stomachs of the Tilapia four hours post feeding, implying that the fluorescent protein was not degraded in the acidic environment of the stomach. Furthermore, clear fluorescence of the protein was also observed in the intestine (FIG. 12). In summary, these results show that the protein is not degraded in the acidic environment of the stomach; it is delivered from the microalgae into the fish intestine; and furthermore, the protein keeps its biological function under these conditions.

Example 8: GFP Absorption by Shrimp

Figure 13B:
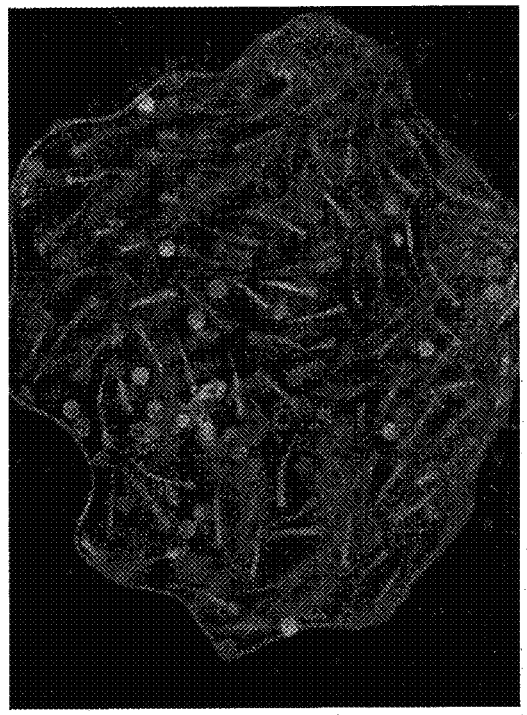
FIGS. 13A-13B show fluorescence imaging of cultures of Brine Shrimp Artemia fed with wild type (FIG. 13A) and vacuole targeted GFP expressing algae (FIG. 13B). Pictures were taken 4 hours post feeding under fluorescent light.
Figure 13A:
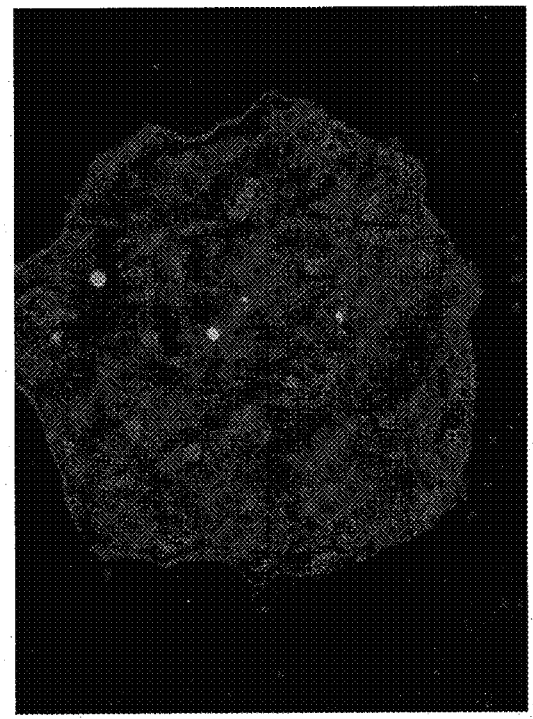

The Brine shrimp *Artemia* were fed with wild type algae (*Phaeodactylum tricornutum*) alone or with algae expressing GFP targeted to the vacuole (vacuole-GFP expressing algae) alone for 3 days post hatching. 8000 *Artemia* grown in 1×ASW medium were fed with $1.5*10^9$ algae. 4 hours post feeding, *Artemia* were carefully washed and analyzed under fluorescent light. FIG. 13 demonstrates that the GFP protein expressed in algae is located within the digestive system of the *Artemia* in its intact and biological form (FIG. 13B). These results again demonstrate that the microalgae system disclosed in the present invention is highly suitable for oral delivery of proteins, which are delivered from the microalgae and into the recipient digestive system in their intact and biologically active form.

Figure 14B:
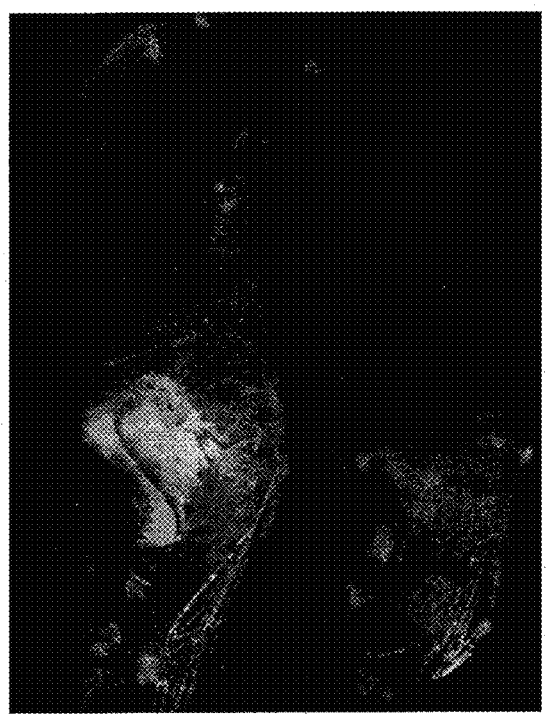
FIGS. 14A-14B show pictures of shrimps Macrobrachium rosenbergii fed with wild type (WT) and vacuole targeted GFP expressing algae taken under bright (FIG. 14A) and fluorescent (FIG. 14B) light.
Figure 14A:

In still additional experiment, starved fresh water shrimps, *Macrobrachium rosenbergii*, PL 10, were fed with pellets composed of regular food mixed with powder of wild-type algae (*Phaeodactylum tricornutum*) or with powder of vacuole-GFP expressing algae in food to algae ratio of 1:1. Shrimps were analyzed under fluorescent light 4 h post feeding. FIG. 14 demonstrates that the GFP protein is located in the hepatopancrease gland of the shrimp, implying oral delivery of the GFP protein in this animal. Again the protein was delivered intact and active.

Example 9: GFP Absorption by Chickens

Figure 15A:
FIGS. 15A-15B show pictures of livers isolated from chicks fed with wild type (WT) and vacuole-targeted GFP expressing algae taken under bright (FIG. 15A) and fluorescent (FIG. 15B) light 6 hours post feeding.
Figure 15B:
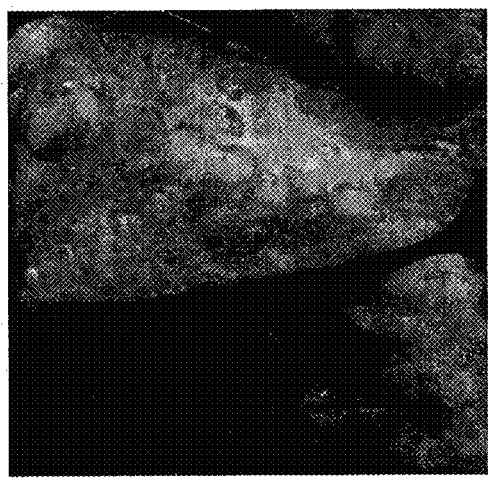

Two weeks old chickens were force fed each with 100 mg of powder of wild-type algae (*Phaeodactylum tricornutum*) or with algae expressing GFP targeted to the vacuole suspended in 5 ml of 0.5× artificial sea water (ASW). Chickens were sacrificed 2, 4, 6 and 24 h post feeding and livers were taken out and analyzed under fluorescent light. FIG. 15 demonstrates that the GFP protein was absorbed into the chick's liver, 6 h post feeding, in its intact and functional form implying that the GFP protein passed through the acidic digestive tract, followed by absorption through the intestine wall into the blood, circulating to the liver. The result demonstrates the full path of protein oral delivery to chickens.

Example 10: Oral Delivery of Proteins to Fish Blood

Tilapia fish were fed with algae (*Phaeodactylum tricornutum*) expressing fish growth hormone or with algae expressing GFP (both targeted to the algae vacuole; vacuole-fGH expressing and vacuole-GFP expressing algae, respectively). 800 mg of algal powder was suspended in 30 ml of 0.5×ASW. Each fish was force-fed with 2 ml algal suspension. Blood samples were taken from the caudal vein using sterile syringes and tubes. Fifty microliters (µl) of each of the blood samples were allocated for direct fluorescence analysis for the activity of GFP in a fluorescence plate reader and the rest of the samples were left to stand for 15 minutes at room temperature, and after an overnight period at 4° C., sera were separated by centrifugation at 250 g for 10 minutes at 4° C., and stored in sterile tubes at −20° C. for ELISA analysis.

Absorption of fGH in Tilapia fish

Tilapia fish were force-fed with vacuole-fGH (construct 398) or vacuole-GFP expressing algae (construct 527). Blood samples were taken 1 h post feeding for ELISA analysis. The presence of the fGH protein was confirmed by detecting the expression of the HA domain, which is fused to the fGH using anti-HA antibody (see Materials and Methods hereinabove). The blood samples taken from fish fed with vacuole-fGH expressing algae, reacted positively with the anti-HA antibody, while blood samples taken from fish fed with vacuole-GFP expressing algae gave non-significant signal (FIG. 16). The ELISA results provide support for the presence of fGH protein in the blood, showing that proteins expressed in the algae reach the blood of organisms orally consuming the algae.

Absorption and Activity of GFP in Tilapia Fish

Tilapia fish (n=5) were force-fed with vacuole-GFP expressing algae (construct 527) or with vacuole-fGH expressing algae (construct 398). Blood sample were collected one hour post feeding and analyzed under fluorescence light (excitation 480 nm, emission 515 nm) using Enspire 2300 multi-label reader. Blood samples collecting from fish def with vacuole-GFP expressing algae exhibited fluorescence. In contrast, blood samples of fish fed with vacuole-fGH expressing algae (construct 398) gave non-significant signal (FIG. 17). The results indicate that GFP was absorbed from the fish intestine into its blood in an intact and functional form.

Figure 18A:
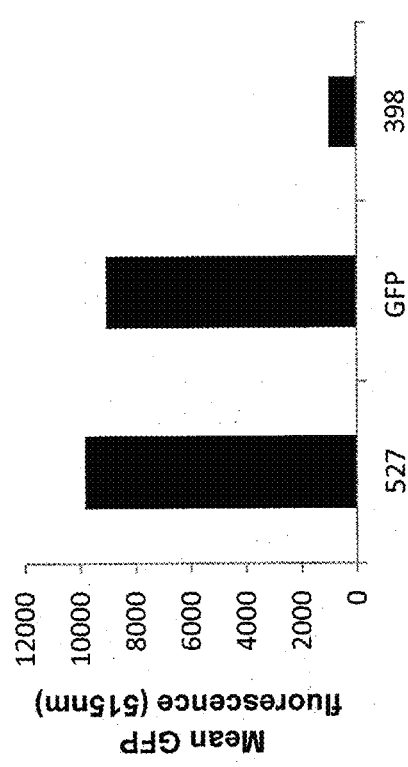
FIGS. 18A-18B demonstrate that exogenous proteins targeted to the alga cell vacuole are protected from degradation in fish gastrointestinal tract.
Figure 18B:
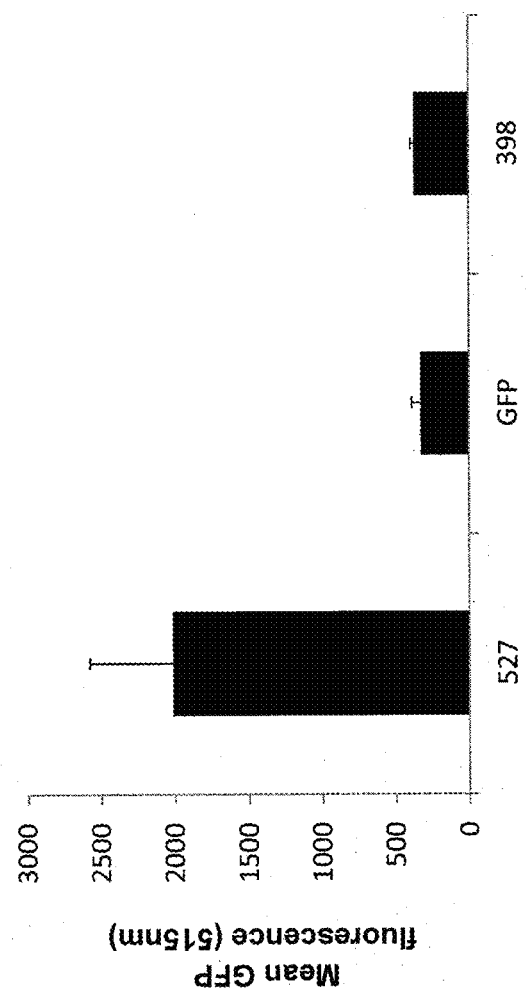

Example 11: Vacuole-Targeted Exogenous Proteins are Protected in the Gastrointestinal Tract Vacuole-GFP and vacuole-fGH expressing algae (harboring construct 527 and 398, respectively) and total protein extracted from the vacuole-GFP expressing algae line were measured for GFP fluorescence before being administered to the fish by force feeding (FIG. 18A) and in blood sample taken from the fish 1 h post application (FIG. 18B). Fluorescence was measured using Enspire 2300 multi-label reader (excitation 480 nm, emission 515 nm). As can be seen, only the blood samples taken from fish fed with GFP expressing algae were fluorescent, while blood samples taken from fish fed with isolated proteins extracted from the vacuole-GFP expressing algae gave no signal or only a background signal as observed in blood samples taken from fish fed with vacuole-fGH expressing algae. The results clearly demonstrate that the algae cell protects the GFP protein and enables its delivery to the blood of the organism consuming the algae in its intact and functional form. In contrast, oral administration of naked fluorescent protein (GFP) leads to abolishment of its fluorescence, probably due to its degradation in the gastro-intestinal tract.

Example 12: Oral Delivery of Proteins to Mice

Delivery of fGH into Mice Liver 12 weeks old balb-C male mice were starved for 12 hours prior to the experiment. Mice were lightly anesthetized using Isoflurane, and fed with 1.5 ml of vacuole-fGH expressing algae (construct 398) or vacuole-GFP expressing algae (construct 527) by gavage-feeding.

Figure 19:
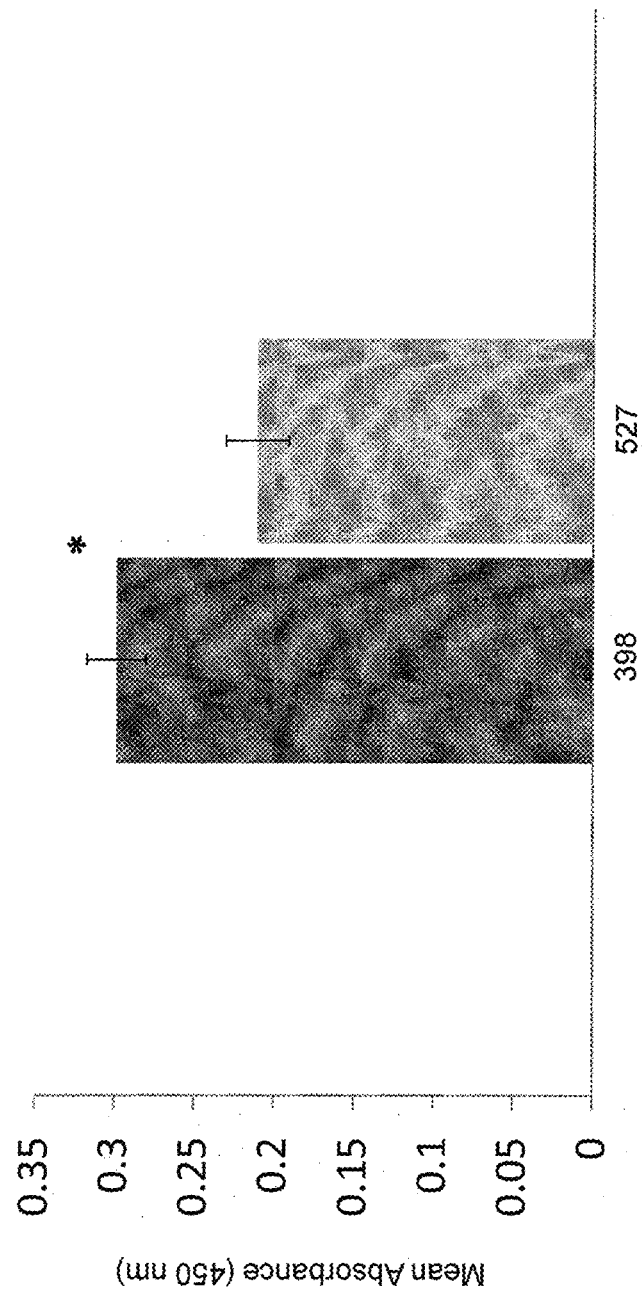
FIG. 19 demonstrates that exogenous fGH targeted to the algae cell vacuole reach the blood and liver of mice fed with the algae. Mice were fed with vacuole-fGH expressing algae (construct 398) or vacuole-GFP expressing algae (construct 527). Level of fGH in the liver was determined using ELISA directed specifically against the recombinant fGH. Results are shown as mean±SD.

Two hours post algal administration mice were euthanized by overdose of isoflurane. Livers were removed and frozen in liquid nitrogen. Total protein was extracted from the livers, followed by ELISA analysis directed towards the HA tag, recognizing specifically the recombinant fGH, expressed in the algae. The ELISA results, shown in FIG. 19, demonstrate that the recombinant fGH was detectable in the mice livers, indicating its oral pass through the mice digestive tract into the blood and the liver.

Absorption of GFP to the Blood

Mice were treated as above, and blood samples were taken from the heart 2 hours post feeding. The blood samples were then centrifuged and the plasma was analyzed under fluorescent light (excitation 480 nm, emission 515 nm). Blood samples of mice fed with vacuole-GFP expressing algae showed significantly higher fluorescence compared to blood samples of mice fed with vacuole-fGH expressing algae, demonstrating the passage of the GFP from the digestive tract into the blood in an intact and functional form.

Example 13: Enhanced Protein Absorption by Fish and Mice

CPPs are short peptides that facilitate cellular uptake of various molecular cargos. Examples of CPPs include the trans-activating transcriptional activator (TAT) from Human Immunodeficiency virus 1 (HIV-1) and the membrane translocating sequence (MTS) from a fibroblast growth factor. The constructs comprising the gene encoding fGH targeted to the vacuole or the gene encoding GFP targeted to the vacuole were further designed to include one of the CPPs as described in the "material and methods" section hereinabove.

Algae lines expressing the vacuole-fGH-MTS-HA or vacuole-fGH-TAT-HA are used to feed fish in feeding trials as described above. Alga lines transformed with the above-constructs wherein the fGH is replaced by GFP (vacuole-GFP-MTS- or vacuole-GFP-TAT-) are used as a model system. Additionally these algae lines are used to feed mice by gavage. At the end of the feeding trials the presence of the algae-expressed protein is examined in blood of the fish or mice fed with the algae using ELISA or Western blot analysis directed toward the HA tag. Additionally, GFP fluorescence of blood samples is detected directly by a fluorescence plate reader or GFP protein is detected by ELISA using an anti GFP antibody.

The results presented above demonstrate that the algae *Phaeodactylum tricornutum* serves as an efficient means to orally deliver recombinant proteins to various target animals. Without wishing to be bound by any specific theory or mechanism of action, the algae serve as a native bio-encapsulation, with the algae cell wall protecting the recombinant protein from its enzymatic degradation in the acidic stomach. The results further suggest, again without wishing to be bound by any specific theory or mechanism of action, that the vacuole targeted protein enables its efficient absorption from the intestine to the target organelle.

In summary, the present application demonstrates for the first time the establishment of an algae based platform, which enables oral administration of recombinant proteins to animals in their intact and functional form.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for oral delivery of a biologically active exogenous protein to a subject, the method comprising orally administering to the subject an effective amount of an edible transgenic *Phaeodactylum tricornutum* microalga or a composition comprising same, wherein the subject is selected from an aquatic animal and a land farm animal, and wherein the transgenic *P. tricornutum* microalga comprises: an expression cassette comprising at least one transcribable polynucleotide encoding the biologically active exogenous protein operatively linked to a vacuole targeting peptide having the amino acid sequence of SEQ ID NO:4, wherein the polynucleotide is operably linked to an expression control sequences; and wherein the expressed biologically active exogenous protein is targeted to the microalga cell vacuole.

2. The method of claim 1, wherein the vacuole targeting peptide is encoded by a polynucleotide comprising the nucleic acid sequence set forth in SEQ ID NO:18.

3. The method of claim 2, wherein the exogenous protein affects at least one of growth, development, and survival of the subject.

4. The method of claim 1, wherein the expression cassette further comprises a polynucleotide encoding a cell penetrating peptide (CPP) that mediates the uptake of the expressed exogenous protein by a cell or a tissue of the subject, operably linked to the polynucleotide encoding said exogenous protein.

5. The method of claim 1, wherein the biologically active exogenous protein has a molecular weight of up to 150 kDa.

6. The method of claim 1, wherein the exogenous biologically active protein has a therapeutic effect on the subject.

7. The method of claim 1, wherein the exogenous biologically active protein enhances at least one of: the growth, the survival, and the reproduction rate of the subject.

8. The method of claim 1, wherein the exogenous biologically active protein is a hormone.

9. The method of claim 8, wherein the hormone is selected from the group consisting of a growth hormone, an appetite inducing hormone and a spawning hormone.

10. The method of claim 9, wherein the hormone is Salmon growth hormone having the amino acid sequence set forth in SEQ ID NO:12.

11. The method of claim 9, wherein the hormone is a spawning hormone having the amino acid sequence set forth in SEQ ID NO:24.

12. The method of claim 9, wherein the hormone is appetite inducing hormone having the amino acid sequence set forth in SEQ ID NO:20.

13. The method of claim 1, wherein the aquatic animal is selected from the group consisting of fish, crustaceans, mollusks and corals.

14. The method of claim 13, wherein the aquatic animal is a fish.

15. The method of claim 1, wherein the land farm animal is selected from the group consisting of poultry, pig, cow and rabbit.

16. The method of claim 15, wherein the land farm animal is poultry.

17. The method of claim 15, wherein the land farm animal is a pig.

* * * * *

SEQUENCE LISTING

```
<160> NUMBER OF SEQ ID NOS: 47

<210> SEQ ID NO 1
<211> LENGTH: 567
<212> TYPE: DNA
<213> ORGANISM: Artificial Sequence
<220> FEATURE:
<223> OTHER INFORMATION: Synthetic Polynucleotide (Salmon growth hormone
      in Phaeodactylum tricornutum codon usage)

<400> SEQUENCE: 1
atgattgaaa accagcgttt gttcaacatt gccgtctccc gtgtccagca cctccacctc      60
ttggcccaga agatgttcaa cgacttcgac ggaaccctcc tccccgacga acgtcgtcag     120
ctcaacaaga ttttcctcct cgacttctgc aactccgact ccattgtctc cccgtcgac      180 aagcacgaaa cccagaagtc ctccgtcctc aagctcctcc acatttcctt ccgcctcatc     240
```

```
gaatcctggg aataccoctc ccagaccctc attatttcca actccctcat ggtccgcaac      300
gccaaccaga tttccgaaaa gctctccgat ctcaaggtcg gaatcaacct cctcattacc      360
ggttcccagg acggactcct ctccctcgac gacaacgact cccagcagct cccccctac      420 ggaaactact accagaacct cggaggcgac ggaaacgtcc gtcgtaacta cgaactcctc      480
gcctgcttca agaaggacat gcacaaggtc gaaacctacc tcaccgtcgc caagtgccgc      540
aagtccctcg aagccaactg caccctc                                          567
```

```
<210> SEQ ID NO 2
<211> LENGTH: 33
<212> TYPE: PRT
<213> ORGANISM: Artificial Sequence
<220> FEATURE:
<223> OTHER INFORMATION: Synthetic Peptide (Phaeodactylum tricornutum
      Endoplasmic reticulum Leader Sequence)

<400> SEQUENCE: 2

Met Met Phe Met Arg Ile Ala Val Ala Ala Leu Ala Leu Leu Ala Ala
1               5                   10                  15

Pro Ser Ile Arg Ala Glu Glu Ala Gly Glu Glu Ala Lys Met Gly Thr
            20                  25                  30

Val

<210> SEQ ID NO 3
<211> LENGTH: 221
<212> TYPE: PRT
<213> ORGANISM: Artificial Sequence
<220> FEATURE:
<223> OTHER INFORMATION: Synthetic Polypeptide

<400> SEQUENCE: 3

Met Met Phe Met Arg Ile Ala Val Ala Ala Leu Ala Leu Leu Ala Ala
1               5                   10                  15

Pro Ser Ile Arg Ala Glu Glu Ala Gly Glu Glu Ala Lys Met Gly Thr
            20                  25                  30

Val Ile Glu Asn Gln Arg Leu Phe Asn Ile Ala Val Ser Arg Val Gln
        35                  40                  45

His Leu His Leu Leu Ala Gln Lys Met Phe Asn Asp Phe Asp Gly Thr
    50                  55                  60

Leu Leu Pro Asp Glu Arg Arg Gln Leu Asn Lys Ile Phe Leu Leu Asp
65                  70                  75                  80

Phe Cys Asn Ser Asp Ser Ile Val Ser Pro Val Asp Lys His Glu Thr
                85                  90                  95

Gln Lys Ser Ser Val Leu Lys Leu Leu His Ile Ser Phe Arg Leu Ile
            100                 105                 110

Glu Ser Trp Glu Tyr Pro Ser Gln Thr Leu Ile Ile Ser Asn Ser Leu
        115                 120                 125

Met Val Arg Asn Ala Asn Gln Ile Ser Glu Lys Leu Ser Asp Leu Lys
    130                 135                 140

Val Gly Ile Asn Leu Leu Ile Thr Gly Ser Gln Asp Gly Leu Leu Ser
145                 150                 155                 160

Leu Asp Asp Asn Asp Ser Gln Gln Leu Pro Pro Tyr Gly Asn Tyr Tyr
                165                 170                 175

Gln Asn Leu Gly Gly Asp Gly Asn Val Arg Arg Asn Tyr Glu Leu Leu
            180                 185                 190

Ala Cys Phe Lys Lys Asp Met His Lys Val Glu Thr Tyr Leu Thr Val
        195                 200                 205
```

```
Ala Lys Cys Arg Lys Ser Leu Glu Ala Asn Cys Thr Leu
    210                 215                 220
```

<210> SEQ ID NO 4
<211> LENGTH: 22
<212> TYPE: PRT
<213> ORGANISM: Artificial Sequence
<220> FEATURE:
<223> OTHER INFORMATION: Synthetic Peptide (Phaeodactylum tricornutum
      Short Vacuole Leader Sequence)

<400> SEQUENCE: 4

```
Met Ser Ile Arg Leu Phe Ser Thr Ala Leu Leu Ala Ala Cys Leu Ala
1               5                   10                  15

Lys Ala Thr Ala Gln Thr
            20
```

<210> SEQ ID NO 5
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 5

```
Tyr Pro Tyr Asp Val Pro Asp Tyr Ala Gly Tyr Pro Tyr Asp Val Pro
1               5                   10                  15

Asp Tyr Ala Gly Ser Tyr Pro Tyr Asp Val Pro Asp Tyr Ala Ala Gln
            20                  25                  30
```

<210> SEQ ID NO 6
<211> LENGTH: 251
<212> TYPE: PRT
<213> ORGANISM: Artificial Sequence
<220> FEATURE:
<223> OTHER INFORMATION: Synthetic Polypeptide

<400> SEQUENCE: 6

```
Met Ser Ile Arg Leu Phe Ser Thr Ala Leu Leu Ala Ala Cys Leu Ala
1               5                   10                  15

Lys Ala Thr Ala Gln Thr Gly Ser Ile Glu Asn Gln Arg Leu Phe Asn
            20                  25                  30

Ile Ala Val Ser Arg Val Gln His Leu His Leu Leu Ala Gln Lys Met
        35                  40                  45

Phe Asn Asp Phe Asp Gly Thr Leu Leu Pro Glu Arg Arg Gln Leu
    50                  55                  60

Asn Lys Ile Phe Leu Leu Asp Phe Cys Asn Ser Asp Ser Ile Val Ser
65                  70                  75                  80

Pro Val Asp Lys His Glu Thr Gln Lys Ser Ser Val Leu Lys Leu Leu
                85                  90                  95

His Ile Ser Phe Arg Leu Ile Glu Ser Trp Glu Tyr Pro Ser Gln Thr
            100                 105                 110

Leu Ile Ile Ser Asn Ser Leu Met Val Arg Asn Ala Asn Gln Ile Ser
        115                 120                 125

Glu Lys Leu Ser Asp Leu Lys Val Gly Ile Asn Leu Leu Ile Thr Gly
    130                 135                 140

Ser Gln Asp Gly Leu Leu Ser Leu Asp Asp Asn Asp Ser Gln Gln Leu
145                 150                 155                 160

Pro Pro Tyr Gly Asn Tyr Gln Asn Leu Gly Gly Asp Gly Asn Val
                165                 170                 175
```

```
Arg Arg Asn Tyr Glu Leu Leu Ala Cys Phe Lys Lys Asp Met His Lys
            180                 185                 190

Val Glu Thr Tyr Leu Thr Val Ala Lys Cys Arg Lys Ser Leu Glu Ala
        195                 200                 205

Asn Cys Thr Leu Arg Ser Gly Gly Gly Gly Tyr Pro Tyr Asp Val
210                 215                 220

Pro Asp Tyr Ala Gly Tyr Pro Tyr Asp Val Pro Asp Tyr Ala Gly Ser
225                 230                 235                 240

Tyr Pro Tyr Asp Val Pro Asp Tyr Ala Ala Gln
                245                 250

<210> SEQ ID NO 7
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 7

Ala Ala Val Leu Leu Pro Val Leu Leu Ala Ala Pro
1               5                   10

<210> SEQ ID NO 8
<211> LENGTH: 265
<212> TYPE: PRT
<213> ORGANISM: Artificial Sequence
<220> FEATURE:
<223> OTHER INFORMATION: Synthetic Polypeptide

<400> SEQUENCE: 8

Met Ser Ile Arg Leu Phe Ser Thr Ala Leu Ala Ala Cys Leu Ala
1               5                   10                  15

Lys Ala Thr Ala Gln Thr Gly Ser Ile Glu Asn Gln Arg Leu Phe Asn
            20                  25                  30

Ile Ala Val Ser Arg Val Gln His Leu His Leu Ala Gln Lys Met
        35                  40                  45

Phe Asn Asp Phe Asp Gly Thr Leu Leu Pro Asp Glu Arg Arg Gln Leu
    50                  55                  60

Asn Lys Ile Phe Leu Leu Asp Phe Cys Asn Ser Asp Ser Ile Val Ser
65                  70                  75                  80

Pro Val Asp Lys His Glu Thr Gln Lys Ser Ser Val Leu Lys Leu Leu
                85                  90                  95

His Ile Ser Phe Arg Leu Ile Glu Ser Trp Glu Tyr Pro Ser Gln Thr
            100                 105                 110

Leu Ile Ile Ser Asn Ser Leu Met Val Arg Asn Ala Asn Gln Ile Ser
        115                 120                 125

Glu Lys Leu Ser Asp Leu Lys Val Gly Ile Asn Leu Leu Ile Thr Gly
    130                 135                 140

Ser Gln Asp Gly Leu Leu Ser Leu Asp Asp Asn Asp Ser Gln Gln Leu
145                 150                 155                 160

Pro Pro Tyr Gly Asn Tyr Tyr Gln Asn Leu Gly Gly Asp Gly Asn Val
                165                 170                 175

Arg Arg Asn Tyr Glu Leu Leu Ala Cys Phe Lys Lys Asp Met His Lys
            180                 185                 190

Val Glu Thr Tyr Leu Thr Val Ala Lys Cys Arg Lys Ser Leu Glu Ala
        195                 200                 205

Asn Cys Thr Leu Arg Ser Ala Ala Val Leu Leu Pro Val Leu Leu Ala
```

```
            210                 215                 220
Ala Pro Arg Ser Gly Gly Gly Gly Tyr Pro Tyr Asp Val Pro Asp
225                 230                 235                 240

Tyr Ala Gly Tyr Pro Tyr Asp Val Pro Asp Tyr Ala Gly Ser Tyr Pro
                245                 250                 255

Tyr Asp Val Pro Asp Tyr Ala Ala Gln
            260                 265

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Tyr Gly Arg Lys Lys Arg Arg Gln Arg Arg Arg
1               5                   10

<210> SEQ ID NO 10
<211> LENGTH: 277
<212> TYPE: PRT
<213> ORGANISM: Artificial Sequence
<220> FEATURE:
<223> OTHER INFORMATION: Synthetic Polypeptide

<400> SEQUENCE: 10

Met Ser Ile Arg Leu Phe Ser Thr Ala Leu Ala Ala Cys Leu Ala
1               5                   10                  15

Lys Ala Thr Ala Gln Thr Gly Ser Ile Glu Asn Gln Arg Leu Phe Asn
                20                  25                  30

Ile Ala Val Ser Arg Val Gln His Leu His Leu Leu Ala Gln Lys Met
            35                  40                  45

Phe Asn Asp Phe Asp Gly Thr Leu Leu Pro Asp Glu Arg Arg Gln Leu
        50                  55                  60

Asn Lys Ile Phe Leu Leu Asp Phe Cys Asn Ser Asp Ser Ile Val Ser
65                  70                  75                  80

Pro Val Asp Lys His Glu Thr Gln Lys Ser Ser Val Leu Lys Leu Leu
                85                  90                  95

His Ile Ser Phe Arg Leu Ile Glu Ser Trp Glu Tyr Pro Ser Gln Thr
            100                 105                 110

Leu Ile Ile Ser Asn Ser Leu Met Val Arg Asn Ala Asn Gln Ile Ser
        115                 120                 125

Glu Lys Leu Ser Asp Leu Lys Val Gly Ile Asn Leu Leu Ile Thr Gly
130                 135                 140

Ser Gln Asp Gly Leu Leu Ser Leu Asp Asp Asn Asp Ser Gln Gln Leu
145                 150                 155                 160

Pro Pro Tyr Gly Asn Tyr Tyr Gln Asn Leu Gly Gly Asp Gly Asn Val
                165                 170                 175

Arg Arg Asn Tyr Glu Leu Leu Ala Cys Phe Lys Lys Asp Met His Lys
            180                 185                 190

Val Glu Thr Tyr Leu Thr Val Ala Lys Cys Arg Lys Ser Leu Glu Ala
        195                 200                 205

Asn Cys Thr Leu Arg Ser Tyr Gly Arg Lys Lys Arg Arg Gln Arg Arg
210                 215                 220

Arg Arg Ser Tyr Gly Arg Lys Lys Arg Gln Arg Arg Arg Ser
225                 230                 235                 240
```

Gly Gly Gly Gly Gly Tyr Pro Tyr Asp Val Pro Asp Tyr Ala Gly Tyr
                245                 250                 255

Pro Tyr Asp Val Pro Asp Tyr Ala Gly Ser Tyr Pro Tyr Asp Val Pro
            260                 265                 270

Asp Tyr Ala Ala Gln
        275

<210> SEQ ID NO 11
<211> LENGTH: 4095
<212> TYPE: DNA
<213> ORGANISM: Artificial Sequence
<220> FEATURE:
<223> OTHER INFORMATION: Synthetic Polynucleotide (pPhaT1 algae
      expression vector)

<400> SEQUENCE: 11

| | |
|---|---:|
| gggctgcagg acgcaatgga ggattatcac cgcaaaaatg aacttcgaaa aaaactttcg | 60 |
| agcgaccatg gaaaaggagg atcagattca gattacaaca gtggattgct ctggtagcaa | 120 |
| atatcttctg ctagattggc tcatggtcgg ttttggacgt tcgaagctca ccgtcaaaag | 180 |
| aaacaaaaga gaagaatgac gtcttcgtga cgtagaatct acgactgtac tcggatctgg | 240 |
| gaaatgaatt gactcacggt cttcttcgag tcctgttaca ggcccttggt ccgaacccc | 300 |
| acacgatttt tgcaccaaag atttgcttca atttgctgga tgttttgact gcaagatcag | 360 |
| ctggcctagc aagagtgctc gtgttgcttc gtcgggaatc cctacgaatt cagttctgc | 420 |
| acaaatttgt ctgccgtttc gagaattcga tatcatcgac taattcgagc tcggtacccg | 480 |
| gggatcctct agagtcgacc tgcaggcatg caagcttcag aagcgtgcta tcgaactcaa | 540 |
| ccagggacgt gcggcacaaa tgggcatcct tgctctcatg gtgcacgaac agttgggagt | 600 |
| ctctatcctt ccttaaaaat ttaattttca ttagttgcag tcactccgct ttggtttcac | 660 |
| agtcaggaat aacactagct cgtcttcacc atggatgcca atctcgccta ttcatggtgt | 720 |
| ataaaagttc aacatccaaa gctagaactt ttggaaagag aaagaatatc cgaatagggc | 780 |
| acggcgtgcc gtattgttgg agtggactag cagaaagtga ggaaggcaca ggatgagttt | 840 |
| tctcgagaca taccttcagc gtcgtcttca ctgtcacagt caactgacag taatcgttga | 900 |
| tccggagaga ttcaaaattc aatctgtttg gacctggata agacacaaga gcgacatcct | 960 |
| gacatgaacg ccgtaaacag caaatcctgg ttgaacacgt atccttttgg gggcctccgc | 1020 |
| tacgacgctc gctccagctg ggcttcctt actatacaca gcgcgcatat ttcacggttg | 1080 |
| ccagatgtca agatggccaa gttgaccagt gccgttccgg tgctcaccgc gcgcgacgtc | 1140 |
| gccggagcgg tcgagttctg gaccgaccgg ctcgggttct cccgggactt cgtggaggac | 1200 |
| gacttcgccg gtgtggtccg ggacgacgtg accctgttca tcagcgcggt ccaggaccag | 1260 |
| gtggtgccgg acaacaccct ggcctgggtg tgggtgcgcg gcctggacga gctgtacgcc | 1320 |
| gagtggtcgg aggtcgtgtc cacgaacttc cgggacgcct ccgggccggc catgaccgag | 1380 |
| atcggcgagc agccgtgggg gcgggagttc gccctgcgcg accggccgg caactgcgtg | 1440 |
| cacttcgtgg ccgaggagca ggactgaacc ttccttaaaa atttaatttt cattagttgc | 1500 |
| agtcactccg ctttggtttc acagtcagga ataacactag ctcgtcttca ccatggatgc | 1560 |
| caatctcgcc tattcatggt gtataaaagt tcaacatcca agctagaac ttttggaaag | 1620 |
| agaaagaata tccgaatagg gcacggcgtg ccgtattgtt ggagtggact agcagaaagt | 1680 |
| gaggaaggca caggatgagt tttctcgagg ccggtctccc tatagtgagt cgtattaatt | 1740 |
| tcgataagcc aggttaacct gcattaatga atcggccaac gcgcggggag aggcggtttg | 1800 |

```
cgtattgggc gctcttccgc ttcctcgctc actgactcgc tgcgctcggt cgttcggctg    1860
cggcgagcgg tatcagctca ctcaaaggcg gtaatacggt tatccacaga atcagggggat   1920 aacgcaggaa agaacatgtg agcaaaaggc cagcaaaagg ccaggaaccg taaaaaggcc    1980
gcgttgctgg cgtttttcca taggctccgc cccctgacg agcatcacaa aaatcgacgc     2040
tcaagtcaga ggtggcgaaa cccgacagga ctataaagat accaggcgtt tccccctgga    2100
agctccctcg tgcgctctcc tgttccgacc ctgccgctta ccggatacct gtccgccttt    2160
ctcccttcgg gaagcgtggc gctttctcaa tgctcacgct gtaggtatct cagttcggtg    2220
taggtcgttc gctccaagct gggctgtgtg cacgaacccc ccgttcagcc cgaccgctgc    2280
gccttatccg gtaactatcg tcttgagtcc aacccggtaa gacacgactt atcgccactg    2340
gcagcagcca ctggtaacag gattagcaga gcgaggtatg taggcggtgc tacagagttc    2400
ttgaagtggt ggcctaacta cggctacact agaaggacag tatttggtat ctgcgctctg    2460
ctgaagccag ttaccttcgg aaaaagagtt ggtagctctt gatccggcaa acaaaccacc    2520
gctggtagcg gtggtttttt tgtttgcaag cagcagatta cgcgcagaaa aaaggatct    2580 caagaagatc ctttgatctt ttctacgggg tctgacgctc agtggaacga aaactcacgt    2640
taagggattt tggtcatgag attatcaaaa aggatcttca cctagatcct tttaaattaa    2700
aaatgaagtt ttaaatcaat ctaaagtata tatgagtaaa cttggtctga cagttaccaa    2760
tgcttaatca gtgaggcacc tatctcagcg atctgtctat ttcgttcatc catagttgcc    2820 tgactcccg tcgtgtagat aactacgata cgggagggct taccatctgg ccccagtgct    2880
gcaatgatac cgcgagaccc acgctcaccg gctccagatt tatcagcaat aaaccagcca    2940
gccggaaggg ccgagcgcag aagtggtcct gcaactttat ccgcctccat ccagtctatt    3000
aattgttgcc gggaagctag agtaagtagt tcgccagtta atagtttgcg caacgttgtt    3060
gccattgcta caggcatcgt ggtgtcacgc tcgtcgtttg gtatggcttc attcagctcc    3120
ggttcccaac gatcaaggcg agttacatga tcccccatgt tgtgcaaaaa agcggttagc    3180
tccttcggtc ctccgatcgt tgtcagaagt aagttggccg cagtgttatc actcatggtt    3240
atggcagcac tgcataattc tcttactgtc atgccatccg taagatgctt ttctgtgact    3300
ggtgagtact caaccaagtc attctgagaa tagtgtatgc ggcgaccgag ttgctcttgc    3360
ccggcgtcaa tacgggataa taccgcgcca catagcagaa ctttaaaagt gctcatcatt    3420
ggaaaacgtt cttcggggcg aaaactctca aggatcttac cgctgttgag atccagttcg    3480
atgtaaccca ctcgtgcacc caactgatct tcagcatctt ttactttcac cagcgtttct    3540
gggtgagcaa aaacaggaag gcaaaatgcc gcaaaaaagg gaataagggc gacacggaaa    3600
tgttgaatac tcatactctt cctttttcaa tattattgaa gcatttatca gggttattgt    3660
ctcatgagcg gatacatatt tgaatgtatt tagaaaaata aacaaatagg ggttccgcgc    3720
acatttcccc gaaaagtgcc acctgacgtc taagaaacca ttattatcat gacattaacc    3780
tataaaaata ggcgtatcac gaggcccttt cgtctcgcgc gtttcggtga tgacggtgaa    3840
aacctctgac acatgcagct cccggagacg gtcacagctt gtctgtaagc ggatgccggg    3900
agcagacaag cccgtcaggg cgcgtcagcg ggtgttggcg ggtgtcgggg ctggcttaac    3960
tatgcggcat cagagcagat tgtactgaga gtgcaccata tggacatatt gtcgttagaa    4020
cgcggctaca attaatacat aaccttatgt atcatacaca tacgatttag gtgacactat    4080
agaaccagat ccccc                                                     4095
```

<210> SEQ ID NO 12
<211> LENGTH: 189
<212> TYPE: PRT
<213> ORGANISM: Artificial Sequence
<220> FEATURE:
<223> OTHER INFORMATION: Synthetic Polypeptide (Mature Salmom Growth Hormone)

<400> SEQUENCE: 12

```
Met Ile Glu Asn Gln Arg Leu Phe Asn Ile Ala Val Ser Arg Val Gln
1               5                   10                  15

His Leu His Leu Leu Ala Gln Lys Met Phe Asn Asp Phe Asp Gly Thr
            20                  25                  30

Leu Leu Pro Asp Glu Arg Arg Gln Leu Asn Lys Ile Phe Leu Leu Asp
        35                  40                  45

Phe Cys Asn Ser Asp Ser Ile Val Ser Pro Val Asp Lys His Glu Thr
    50                  55                  60

Gln Lys Ser Ser Val Leu Lys Leu Leu His Ile Ser Phe Arg Leu Ile
65                  70                  75                  80

Glu Ser Trp Glu Tyr Pro Ser Gln Thr Leu Ile Ile Ser Asn Ser Leu
                85                  90                  95

Met Val Arg Asn Ala Asn Gln Ile Ser Glu Lys Leu Ser Asp Leu Lys
            100                 105                 110

Val Gly Ile Asn Leu Leu Ile Thr Gly Ser Gln Asp Gly Leu Leu Ser
        115                 120                 125

Leu Asp Asp Asn Asp Ser Gln Gln Leu Pro Pro Tyr Gly Asn Tyr Tyr
    130                 135                 140

Gln Asn Leu Gly Gly Asp Gly Asn Val Arg Arg Asn Tyr Glu Leu Leu
145                 150                 155                 160

Ala Cys Phe Lys Lys Asp Met His Lys Val Glu Thr Tyr Leu Thr Val
                165                 170                 175

Ala Lys Cys Arg Lys Ser Leu Glu Ala Asn Cys Thr Leu
            180                 185
```

<210> SEQ ID NO 13
<211> LENGTH: 30
<212> TYPE: PRT
<213> ORGANISM: Artificial Sequence
<220> FEATURE:
<223> OTHER INFORMATION: Synthetic Peptide (Phaeodactylum tricornutum Full Vacuole Leader Sequence)

<400> SEQUENCE: 13

```
Met Ser Ile Arg Leu Phe Ser Thr Ala Leu Leu Ala Ala Cys Leu Ala
1               5                   10                  15

Lys Ala Thr Ala Gln Thr Cys Pro Thr Leu Ile Trp Ser Asp
            20                  25                  30
```

<210> SEQ ID NO 14
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 14
gccgccgtcc tcctccccgt cttgttggct gccccc         36

<210> SEQ ID NO 15
<211> LENGTH: 33

```
<212> TYPE: DNA
<213> ORGANISM: Artificial Sequence
<220> FEATURE:
<223> OTHER INFORMATION: Synthetic Polynucleotide

<400> SEQUENCE: 15
tacggacgta agaagcgtcg tcagcgccgt cgt                                    33

<210> SEQ ID NO 16
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 16
atgatgttca tgagaattgc cgtagcagca ctggccttgc tggctgctcc ctccattcgt       60
gccgaagagg ctggtgaaga ggccaagatg ggtaccgtg                              99

<210> SEQ ID NO 17
<211> LENGTH: 666
<212> TYPE: DNA
<213> ORGANISM: Artificial Sequence
<220> FEATURE:
<223> OTHER INFORMATION: Synthetic Polynucleotide

<400> SEQUENCE: 17
atgatgttca tgagaattgc cgtagcagca ctggccttgc tggctgctcc ctccattcgt       60
gccgaagagg ctggtgaaga ggccaagatg ggtaccgtga ttgaaaacca gcgtttgttc      120
aacattgccg tctcccgtgt ccagcacctc cacctcttgg cccagaagat gttcaacgac      180
ttcgacggaa ccctcctccc cgacgaacgt cgtcagctca caagatttt cctcctcgac       240 ttctgcaact ccgactccat tgtctccccc gtcgacaagc acgaaaccca gaagtcctcc      300
gtcctcaagc cctccacat ttccttccgc ctcatcgaat cctgggaata ccctcccag        360 accctcatta tttccaactc cctcatggtc cgcaacgcca accagatttc cgaaaagctc      420
tccgatctca aggtcggaat caacctcctc attaccggtt cccaggacgg actcctctcc      480
ctcgacgaca acgactccca gcagctcccc ccctacggaa actactacca gaacctcgga      540
ggcgacggaa acgtccgtcg taactacgaa ctcctcgcct gcttcaagaa ggacatgcac      600
aaggtcgaaa cctacctcac cgtcgccaag tgccgcaagt ccctcgaagc caactgcacc      660
ctctaa                                                                  666

<210> SEQ ID NO 18
<211> LENGTH: 67
<212> TYPE: DNA
<213> ORGANISM: Artificial Sequence
<220> FEATURE:
<223> OTHER INFORMATION: Synthetic Polynucleotide

<400> SEQUENCE: 18
atgtcgattc gtctcttctc taccgcctta ctagctgctt gcttagcaaa ggcaactgcc       60
caaactg                                                                  67

<210> SEQ ID NO 19
<211> LENGTH: 756
<212> TYPE: DNA
<213> ORGANISM: Artificial Sequence
<220> FEATURE:
<223> OTHER INFORMATION: Synthetic Polynucleotide
```

<400> SEQUENCE: 19

```
atgtcgattc gtctcttctc taccgcctta ctagctgctt gcttagcaaa ggcaactgcc    60
caaactggat ccattgaaaa ccagcgtttg ttcaacattg ccgtctcccg tgtccagcac   120
ctccacctct tggcccagaa gatgttcaac gacttcgacg gaaccctcct ccccgacgaa   180
cgtcgtcagc tcaacaagat tttcctcctc gacttctgca actccgactc cattgtctcc   240
cccgtcgaca agcacgaaac ccagaagtcc tccgtcctca agctcctcca catttccttc   300
cgcctcatcg aatcctggga ataccccctcc cagaccctca ttatttccaa ctccctcatg   360
gtccgcaacg ccaaccagat ttccgaaaag ctctccgatc tcaaggtcgg aatcaacctc   420
ctcattaccg gttcccagga cggactcctc tccctcgacg acaacgactc ccagcagctc   480
cccccctacg aaactactac cagaacctc ggaggcgacg aaacgtccg tcgtaactac   540 gaactcctcg cctgcttcaa gaaggacatg cacaaggtcg aaacctacct caccgtcgcc   600
aagtgccgca gtccctcga agccaactgc accctcagat ctggtggagg tggcggatac   660
ccgtacgacg tccctgatta cgccggatac ccttacgatg tcccggacta cgccggttcc   720 taccccctacg acgtcccgga ctacgccgcc cagtaa                             756
```

<210> SEQ ID NO 20
<211> LENGTH: 45
<212> TYPE: PRT
<213> ORGANISM: Artificial Sequence
<220> FEATURE:
<223> OTHER INFORMATION: Synthetic peptide (agouti-related protein fragment)

<400> SEQUENCE: 20

```
Cys Ile Pro His Gln Gln Ser Cys Leu Gly His His Leu Pro Cys Cys
1               5                   10                  15

Asn Pro Cys Asp Thr Cys Tyr Cys Arg Phe Phe Lys Ala Phe Cys Tyr
            20                  25                  30

Cys Arg Ser Met Asp Asn Thr Cys Lys Asn Glu Tyr Ala
        35                  40                  45
```

<210> SEQ ID NO 21
<211> LENGTH: 135
<212> TYPE: DNA
<213> ORGANISM: Artificial Sequence
<220> FEATURE:
<223> OTHER INFORMATION: Synthetic Polynucleotide

<400> SEQUENCE: 21

```
tgcattccgc accagcagtc ctgcctcgga caccacctcc cgtgctgcaa cccctgcgac    60
acctgctact gtcgtttctt caaagccttc tgttactgcc gttccatgga caacacctgt   120
aagaacgaat acgcc                                                    135
```

<210> SEQ ID NO 22
<211> LENGTH: 67
<212> TYPE: PRT
<213> ORGANISM: Artificial Sequence
<220> FEATURE:
<223> OTHER INFORMATION: Synthetic Peptide

<400> SEQUENCE: 22

```
Met Ser Ile Arg Leu Phe Ser Thr Ala Leu Leu Ala Ala Cys Leu Ala
1               5                   10                  15

Lys Ala Thr Ala Gln Thr Cys Ile Pro His Gln Gln Ser Cys Leu Gly
            20                  25                  30
```

His His Leu Pro Cys Cys Asn Pro Cys Asp Thr Cys Tyr Cys Arg Phe
            35                  40                  45

Phe Lys Ala Phe Cys Tyr Cys Arg Ser Met Asp Asn Thr Cys Lys Asn
        50                  55                  60

Glu Tyr Ala
65

<210> SEQ ID NO 23
<211> LENGTH: 201
<212> TYPE: DNA
<213> ORGANISM: Artificial Sequence
<220> FEATURE:
<223> OTHER INFORMATION: Synthetic Polynucleotide

<400> SEQUENCE: 23
atgtccatcc gtctcttctc caccgccctc ttggccgcct gcctcgccaa ggccaccgct    60
cagacctgca ttccgcacca gcagtcctgc ctcggacacc acctcccgtg ctgcaacccc   120
tgcgacacct gctactgtcg tttcttcaaa gccttctgtt actgccgttc catggacaac   180
acctgtaaga acgaatacgc c                                             201

<210> SEQ ID NO 24
<211> LENGTH: 10
<212> TYPE: PRT
<213> ORGANISM: Gallus gallus

<400> SEQUENCE: 24

Gln His Trp Ser His Gly Trp Tyr Pro Gly
1               5                   10

<210> SEQ ID NO 25
<211> LENGTH: 30
<212> TYPE: DNA
<213> ORGANISM: Gallus gallus

<400> SEQUENCE: 25
cagcactggt cccacggatg gtaccccgga                                      30

<210> SEQ ID NO 26
<211> LENGTH: 32
<212> TYPE: PRT
<213> ORGANISM: Artificial Sequence
<220> FEATURE:
<223> OTHER INFORMATION: Synthetic Peptide

<400> SEQUENCE: 26

Met Ser Ile Arg Leu Phe Ser Thr Ala Leu Leu Ala Ala Cys Leu Ala
1               5                   10                  15

Lys Ala Thr Ala Gln Thr Gln His Trp Ser His Gly Trp Tyr Pro Gly
            20                  25                  30

<210> SEQ ID NO 27
<211> LENGTH: 255
<212> TYPE: DNA
<213> ORGANISM: Artificial Sequence
<220> FEATURE:
<223> OTHER INFORMATION: Synthetic Polynucleotide

<400> SEQUENCE: 27
atgtccatcc gtctcttctc caccgccctc ttggccgcct gcctcgccaa ggccaccgct    60
cagacccagc actggtccca cggatggtac cccggaggaa agcgtgaact cgactccttt   120

```
ggaacctccg agatttccga agaaattaag ctctgcgagg ccggagaatg ttcctacctc    180
cgtccccagc gccgtggcgt gctccgttcc atcctcttgg acgccctcgc ccgtgaactc    240
caaaagcgta agtga                                                     255
```

<210> SEQ ID NO 28
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 28

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 29
<211> LENGTH: 720
<212> TYPE: DNA
<213> ORGANISM: Artificial Sequence
<220> FEATURE:
<223> OTHER INFORMATION: Synthetic Polynucleotide

<400> SEQUENCE: 29

```
atggtgagca agggcgagga gctgttcacc ggggtggtgc ccatcctggt cgagctggac    60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
```

```
cagcacgact tcttcaagtc cgccatgccc gaaggctacg tccaggagcg caccatcttc      300
ttcaaggacg acggcaacta caagacccgc gccgaggtga agttcgaggg cgacaccctg      360
gtgaaccgca tcgagctgaa gggcatcgac ttcaaggagg acggcaacat cctggggcac      420
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcggc gacggccccg tgctgctgcc cgacaaccac      600
tacctgagca cccagtccgc cctgagcaaa gaccccaacg agaagcgcga tcacatggtc      660
ctgctggagt tcgtgaccgc cgccgggatc actctcggca tggacgagct gtacaagtaa      720
```

<210> SEQ ID NO 30
<211> LENGTH: 263
<212> TYPE: PRT
<213> ORGANISM: Artificial Sequence
<220> FEATURE:
<223> OTHER INFORMATION: Synthetic Polypeptide
<400> SEQUENCE: 30

```
Met Ser Ile Arg Leu Phe Ser Thr Ala Leu Leu Ala Ala Cys Leu Ala
1               5                   10                  15

Lys Ala Thr Ala Gln Thr Gly Ser Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Met Ala Asp Lys Gln Lys Asn Gly Ile Lys Val Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Met Val Leu Leu Glu Phe Val Thr Ala Ala Gly Ile Thr Leu
                245                 250                 255

Gly Met Asp Glu Leu Tyr Lys
            260
```

<210> SEQ ID NO 31

<211> LENGTH: 792
<212> TYPE: DNA
<213> ORGANISM: Artificial Sequence
<220> FEATURE:
<223> OTHER INFORMATION: Synthetic Polynucleotide

<400> SEQUENCE: 31

| | | | | | |
|---|---|---|---|---|---|
| atgtcgattc | gtctcttctc | taccgcctta | ctagctgctt | gcttagcaaa | ggcaactgcc | 60 |
| caaactggat | ccatggtgag | caagggcgag | gagctgttca | ccggggtggt | gcccatcctg | 120 |
| gtcgagctgg | acggcgacgt | aaacggccac | aagttcagcg | tgtccggcga | gggcgagggc | 180 |
| gatgccacct | acggcaagct | gaccctgaag | ttcatctgca | ccaccggcaa | gctgcccgtg | 240 |
| ccctggccca | ccctcgtgac | caccctgacc | tacggcgtgc | agtgcttcag | ccgctacccc | 300 |
| gaccacatga | agcagcacga | cttcttcaag | tccgccatgc | ccgaaggcta | cgtccaggag | 360 |
| cgcaccatct | tcttcaagga | cgacggcaac | tacaagaccc | gcgccgaggt | gaagttcgag | 420 |
| ggcgacaccc | tggtgaaccg | catcgagctg | aagggcatcg | acttcaagga | ggacggcaac | 480 |
| atcctggggc | acaagctgga | gtacaactac | aacagccaca | acgtctatat | catggccgac | 540 |
| aagcagaaga | acggcatcaa | ggtgaacttc | aagatccgcc | acaacatcga | ggacggcagc | 600 |
| gtgcagctcg | ccgaccacta | ccagcagaac | acccccatcg | gcgacggccc | cgtgctgctg | 660 |
| cccgacaacc | actacctgag | cacccagtcc | gccctgagca | agacccccaa | cgagaagcgc | 720 |
| gatcacatgg | tcctgctgga | gttcgtgacc | gccgccggga | tcactctcgg | catggacgag | 780 |
| ctgtacaagt | aa | | | | | 792 |

<210> SEQ ID NO 32
<211> LENGTH: 278
<212> TYPE: PRT
<213> ORGANISM: Artificial Sequence
<220> FEATURE:
<223> OTHER INFORMATION: Synthetic Polypeptide

<400> SEQUENCE: 32

Met Ser Ile Arg Leu Phe Ser Thr Ala Leu Leu Ala Ala Cys Leu Ala
1               5                   10                  15

Lys Ala Thr Ala Gln Thr Gly Ser Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Tyr
    50                  55                  60

Gly Lys Leu Thr Leu Lys Phe Ile Cys Thr Thr Gly Lys Leu Pro Val
65                  70                  75                  80

Pro Trp Pro Thr Leu Val Thr Thr Leu Thr Tyr Gly Val Gln Cys Phe
                85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

```
Ile Met Ala Asp Lys Gln Lys Asn Gly Ile Lys Val Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Met Val Leu Leu Glu Phe Val Thr Ala Ala Gly Ile Thr Leu
                245                 250                 255

Gly Met Asp Glu Leu Tyr Lys Lys Leu Ser Ala Ala Val Leu Leu Pro
            260                 265                 270

Val Leu Leu Ala Ala Pro
            275

<210> SEQ ID NO 33
<211> LENGTH: 838
<212> TYPE: DNA
<213> ORGANISM: Artificial Sequence
<220> FEATURE:
<223> OTHER INFORMATION: Synthetic Polynucleotide

<400> SEQUENCE: 33
atgtcgattc gtctcttctc taccgcctta ctagctgctt gcttagcaaa ggcaactgcc      60
caaactggat ccatggtgag caagggcgag gagctgttca ccggggtggt gcccatcctg     120
gtcgagctgg acggcgacgt aaacggccac aagttcagcg tgtccggcga gggcgagggc     180
gatgccacct acggcaagct gaccctgaag ttcatctgca ccaccggcaa gctgcccgtg     240
ccctggccca cctcgtgac cacccctgacc tacggcgtgc agtgcttcag ccgctacccc     300
gaccacatga agcagcacga cttcttcaag tccgccatgc ccgaaggcta cgtccaggag     360
cgcaccatct tcttcaagga cgacggcaac tacaagaccc gcgccgaggt gaagttcgag     420
ggcgacaccc tggtgaaccg catcgagctg aagggcatcg acttcaagga ggacggcaac     480
atcctggggc acaagctgga gtacaactac aacagccaca acgtctatat catggccgac     540
aagcagaaga acggcatcaa ggtgaacttc aagatccgcc acaacatcga ggacggcagc     600
gtgcagctcg ccgaccacta ccagcagaac ccccatcg cgacggcccc cgtgctgctg     660
cccgacaacc actacctgag cacccagtcc gccctgagca agaccccaa cgagaagcgc     720
gatcacatgg tcctgctgga gttcgtgacc gccgccggga tcactctcgg catggacgag     780
ctgtacaaga agctttctgc cgccgtcctc ctccccgtct tgttggctgc ccccataa     838

<210> SEQ ID NO 34
<211> LENGTH: 276
<212> TYPE: PRT
<213> ORGANISM: Artificial Sequence
<220> FEATURE:
<223> OTHER INFORMATION: Synthetic Polypeptide

<400> SEQUENCE: 34

Met Ser Ile Arg Leu Phe Ser Thr Ala Leu Leu Ala Ala Cys Leu Ala
1               5                  10                  15

Lys Ala Thr Ala Gln Thr Gly Ser Met Val Ser Lys Gly Glu Glu Leu
            20                  25                  30

Phe Thr Gly Val Val Pro Ile Leu Val Glu Leu Asp Gly Asp Val Asn
        35                  40                  45

Gly His Lys Phe Ser Val Ser Gly Glu Gly Glu Gly Asp Ala Thr Tyr
```

```
            50                  55                  60
Gly Lys Leu Thr Leu Lys Phe Ile Cys Thr Thr Gly Lys Leu Pro Val
 65                  70                  75                  80

Pro Trp Pro Thr Leu Val Thr Leu Thr Tyr Gly Val Gln Cys Phe
                 85                  90                  95

Ser Arg Tyr Pro Asp His Met Lys Gln His Asp Phe Phe Lys Ser Ala
            100                 105                 110

Met Pro Glu Gly Tyr Val Gln Glu Arg Thr Ile Phe Phe Lys Asp Asp
        115                 120                 125

Gly Asn Tyr Lys Thr Arg Ala Glu Val Lys Phe Glu Gly Asp Thr Leu
    130                 135                 140

Val Asn Arg Ile Glu Leu Lys Gly Ile Asp Phe Lys Glu Asp Gly Asn
145                 150                 155                 160

Ile Leu Gly His Lys Leu Glu Tyr Asn Tyr Asn Ser His Asn Val Tyr
                165                 170                 175

Ile Met Ala Asp Lys Gln Lys Asn Gly Ile Lys Val Asn Phe Lys Ile
            180                 185                 190

Arg His Asn Ile Glu Asp Gly Ser Val Gln Leu Ala Asp His Tyr Gln
        195                 200                 205

Gln Asn Thr Pro Ile Gly Asp Gly Pro Val Leu Leu Pro Asp Asn His
    210                 215                 220

Tyr Leu Ser Thr Gln Ser Ala Leu Ser Lys Asp Pro Asn Glu Lys Arg
225                 230                 235                 240

Asp His Met Val Leu Leu Glu Phe Val Thr Ala Ala Gly Ile Thr Leu
                245                 250                 255

Gly Met Asp Glu Leu Tyr Lys Lys Leu Tyr Gly Arg Lys Lys Arg Arg
            260                 265                 270

Gln Arg Arg
    275

<210> SEQ ID NO 35
<211> LENGTH: 831
<212> TYPE: DNA
<213> ORGANISM: Artificial Sequence
<220> FEATURE:
<223> OTHER INFORMATION: Synthetic Polynucleotide

<400> SEQUENCE: 35
atgtcgattc gtctcttctc taccgcctta ctagctgctt gcttagcaaa ggcaactgcc      60
caaactggat ccatggtgag caagggcgag gagctgttca ccggggtggt gcccatcctg     120
gtcgagctgg acggcgacgt aaacggccac aagttcagcg tgtccggcga gggcgagggc     180
gatgccacct acggcaagct gaccctgaag ttcatctgca ccaccggcaa gctgcccgtg     240
ccctggccca ccctcgtgac caccctgacc tacggcgtgc agtgcttcag ccgctacccc     300
gaccacatga gcagcacga cttcttcaag tccgccatgc ccgaaggcta cgtccaggag     360
cgcaccatct tcttcaagga cgacggcaac tacaagaccc gcgccgaggt gaagttcgag     420
ggcgacaccc tggtgaaccg catcgagctg aagggcatcg acttcaagga ggacggcaac     480
atcctggggc acaagctgga gtacaactac aacagccaca acgtctatat catggccgac     540
aagcagaaga acggcatcaa ggtgaacttc aagatccgcc acaacatcga ggacggcagc     600
gtgcagctcg ccgaccacta ccagcagaac acccccatcg gcgacggccc cgtgctgctg     660
cccgacaacc actacctgag cacccagtcc gccctgagca agaccccaa cgagaagcgc     720 gatcacatgg tcctgctgga gttcgtgacc gccgcgggga tcactctcgg catggacgag     780
```
ctgtacaaga agctttacgg acgtaagaag cgtcgtcagc gccgtcgtta a     831

<210> SEQ ID NO 36
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 36
ggaattcatg atgttcatga gaattgc     27

<210> SEQ ID NO 37
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 37
acgctggttt tcaatcacgg tacccatctt     30

<210> SEQ ID NO 38
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 38
ggaattcatg atgttcatga gaattgc     27

<210> SEQ ID NO 39
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 39
acgctggttt tcaatcacgg tacccatctt     30

<210> SEQ ID NO 40
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 40
aagatgggta ccgtgattga aaaccagcgt     30

<210> SEQ ID NO 41
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 41
gagatctgag ggtgcagttg g     21

<210> SEQ ID NO 42
<211> LENGTH: 28
<212> TYPE: DNA

<213> ORGANISM: Artificial Sequence
<220> FEATURE:
<223> OTHER INFORMATION: Synthetic Polynucleotide

<400> SEQUENCE: 42
ggaattcatg ggccaagtct ttctcttg                                        28

<210> SEQ ID NO 43
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 43
ggatccattg aaaaccagcg tttgttcaac                                      30

<210> SEQ ID NO 44
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 44
aagcttttac tgggcggcgt agtccggac gtcgtagggg ta                         42

<210> SEQ ID NO 45
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 45
atgaattcat gtcgattcgt ctct                                            24

<210> SEQ ID NO 46
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 46
atggatccag tttgggcagt tgcc                                            24

<210> SEQ ID NO 47
<211> LENGTH: 98
<212> TYPE: DNA
<213> ORGANISM: Artificial Sequence
<220> FEATURE:
<223> OTHER INFORMATION: Synthetic Polynucleotide

<400> SEQUENCE: 47
tacccgtacg acgtccctga ttacgccgga tacccttacg atgtcccgga ctacgccggt    60
tcctacccct acgacgtccc ggactacgcc gcccagta                             98